United States Patent
Choi et al.

(10) Patent No.: US 9,730,665 B2
(45) Date of Patent: Aug. 15, 2017

(54) X-RAY IMAGING APPARATUS AND CONTROL METHOD FOR SEPARATING TISSUE IMAGES

(71) Applicant: SAMSUNG ELECTRONICS CO., LTD., Suwon-si (KR)

(72) Inventors: Jiyoung Choi, Suwon-si (KR); Dong-Goo Kang, Hwaseong-si (KR); Young Hun Sung, Hwaseong-si (KR); Jae Hak Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/730,634

(22) Filed: Jun. 4, 2015

(65) Prior Publication Data

US 2015/0363939 A1 Dec. 17, 2015

(30) Foreign Application Priority Data

Jun. 12, 2014 (KR) ........................ 10-2014-0071291

(51) Int. Cl.
*G06T 7/20* (2017.01)
*G06T 7/00* (2017.01)
*G06T 5/00* (2006.01)
*A61B 6/00* (2006.01)
*A61B 6/02* (2006.01)

(Continued)

(52) U.S. Cl.
CPC .............. *A61B 6/5264* (2013.01); *A61B 6/02* (2013.01); *A61B 6/4241* (2013.01); *G06T 7/223* (2017.01); *G06T 7/269* (2017.01); *G06T 7/30* (2017.01); *A61B 6/482* (2013.01); *G06T 2207/10116* (2013.01); *G06T 2207/20212* (2013.01); *G06T 2207/30008* (2013.01)

(58) Field of Classification Search
None
See application file for complete search history.

(56) References Cited

U.S. PATENT DOCUMENTS

2005/0238218 A1* 10/2005 Nakamura ............ G06T 7/0012
382/128
2010/0067660 A1* 3/2010 Maurer, Jr. .............. A61B 6/12
378/95

(Continued)

FOREIGN PATENT DOCUMENTS

WO    WO 2013111033 A2 *  8/2013    ........... G06F 19/321

OTHER PUBLICATIONS

Szigeti et al., "Motion Based X-Ray Imaging Modality", IEEE Transactions on Medical Imaging, vol. 33, No. 10, Oct. 2014.*

(Continued)

*Primary Examiner* — Jason Heidemann
*Assistant Examiner* — Brian Shin
(74) *Attorney, Agent, or Firm* — Sughrue Mion, PLLC

(57) ABSTRACT

An X-ray imaging apparatus includes an image separator configured to extract a first tissue image having a small amount of motion of a tissue, the small amount of motion being smaller than a threshold amount of motion, and to extract a second tissue image with a large amount of motion of a tissue, the large amount of motion being larger than the small amount of motion, from a plurality of image frames, and an image processor configured to correct the second tissue image according to the large amount of motion of the tissue.

20 Claims, 15 Drawing Sheets

(51) Int. Cl.
*G06T 7/30* (2017.01)
*G06T 7/223* (2017.01)
*G06T 7/269* (2017.01)

(56) References Cited

U.S. PATENT DOCUMENTS

| | | | | |
|---|---|---|---|---|
| 2010/0074490 A1* | 3/2010 | Arakita | ............... | G06T 7/0012 382/128 |
| 2011/0123081 A1* | 5/2011 | Sebok | ................ | A61B 6/032 382/131 |
| 2012/0082350 A1* | 4/2012 | Wollenweber | ......... | A61B 6/463 382/128 |
| 2013/0121555 A1* | 5/2013 | Bruder | ............... | G06T 11/003 382/131 |

OTHER PUBLICATIONS

Feng, "Segmentation of Bone Structures in X-ray Images", School of Computing National University of Singapore, Jul. 2006.*

* cited by examiner

X-RAY IMAGING APPARATUS AND CONTROL METHOD FOR SEPARATING TISSUE IMAGES

CROSS-REFERENCE TO RELATED APPLICATION

This application claims the benefit of Korean Patent Application No. 2014-0071291, filed on Jun. 12, 2014 in the Korean Intellectual Property Office, the disclosure of which is incorporated herein by reference in its entirety.

BACKGROUND

1. Field

Exemplary embodiments of the present disclosure relate to an X-ray imaging apparatus configured to generate an X-ray image by irradiating X-rays onto an object, and a control method of the X-ray imaging apparatus.

2. Description of the Related Art

An X-ray imaging apparatus is equipment for acquiring images about the inside of an object by irradiating X-rays onto the object and receiving the X-rays transmitted through the object. Since various materials configuring an object have different degrees of X-ray radiolucency according to properties of the various materials, the inside structure of the object can be imaged by detecting the strengths or intensities of X-rays transmitted through the object.

More specifically, if an X-ray generator generates X-rays and irradiates the X-rays onto an object, an X-ray detector detects the X-rays transmitted through the object, and converts the detected X-rays into electrical signals. Since converting the X-rays into the electronic signals is performed for individual pixels, electrical signals corresponding to the individual pixels are combined to acquire an X-ray image.

Lately, in order to ensure safety of the X-ray imaging apparatus, there is a trend towards acquiring several low-dose X-ray images to increase a Signal to Noise Radio (SNR) while reducing a dose of X-rays that is irradiated onto an object.

However, when the several low-dose X-ray images are acquired, a motion blur is created in the acquired images due to motions of tissues in the object. Accordingly, studies into a method for reducing such a motion blur are underway.

SUMMARY

Therefore, it is an aspect of the exemplary embodiments to provide an X-ray imaging apparatus configured to correct a frame image according to a motion of each tissue, instead of entirely correcting the frame image, and a control method of the X-ray imaging apparatus.

Additional aspects of the disclosure will be set forth in part in the description which follows and, in part, will be obvious from the description, or may be learned by practice of the exemplary embodiments.

In accordance with an aspect of an exemplary embodiment, there is provided an X-ray imaging apparatus including: an image separator configured to extract a first tissue image having a small amount of motion of a tissue, the small amount of motion being smaller than a threshold amount of motion, and to extract a second tissue image with a large amount of motion of a tissue, the large amount of motion being larger than the small amount of motion, from a plurality of frame images; and an image processor configured to correct the second tissue image according to the large amount of motion of the tissue.

The image processor may be configured to estimate the large amount of motion of the tissue displayed in the second tissue image, and correct the second tissue image according to the estimated motion of the tissue.

The image processor may be configured to combine the corrected second tissue image with the first tissue image to generate a corrected image frame.

The image separator may be configured to extract the second tissue image from an image frame of the plurality of image frames, and extract the first tissue image from another image frame of the plurality of image frames.

The image separator may be configured to extract the second tissue image from an image frame of the plurality of image frames, and remove components of the second tissue image from another image frame of the plurality of image frames to extract the first tissue image.

The X-ray imaging apparatus may further include an image analyzer configured to compare the plurality of image frames to each other to analyze a plurality of motions of a plurality of tissues included in the plurality of image frames.

The image analyzer may be configured to group the analyzed motions of the tissues into a plurality of groups according to predetermined criteria, the image separator may be configured to extract a tissue image for each group, and the image processor may be configured to correct each tissue image using a predetermined correction value according to a group to which the tissue image belongs.

The image analyzer may be configured to calculate a plurality of motion vectors of each tissue, and the image processor may be configured to convert, for each tissue, the motion vectors of the tissue into a motion transform matrix, and correct a tissue image of the tissue using the motion transform matrix.

The image analyzer may be configured to analyze the motions of the tissues using pre-stored tissue data.

The image analyzer may be configured to compare the corrected image frame to the plurality of image frames to analyze a motion of each tissue, the image processor may be configured to correct a tissue image of each tissue according to the analyzed motion of the tissue, and the image analyzer and the image processor may be configured to repeat the operations of comparing the corrected image frame and correcting the tissue image until the image processor determines that the tissue has no motion based on results of comparison between the corrected image frame and the plurality of image frames.

In accordance with an aspect of another exemplary embodiment, there is provided a control method to control an X-ray imaging apparatus, the control method including: extracting a first tissue image with a small amount of motion of a tissue, the small amount of motion being smaller than a threshold amount of motion, and extracting a second tissue image with a large amount of motion of a tissue, the large amount of motion being larger than the small amount of motion, from a plurality of image frames; and correcting the second tissue image according to the large amount of motion of the tissue.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
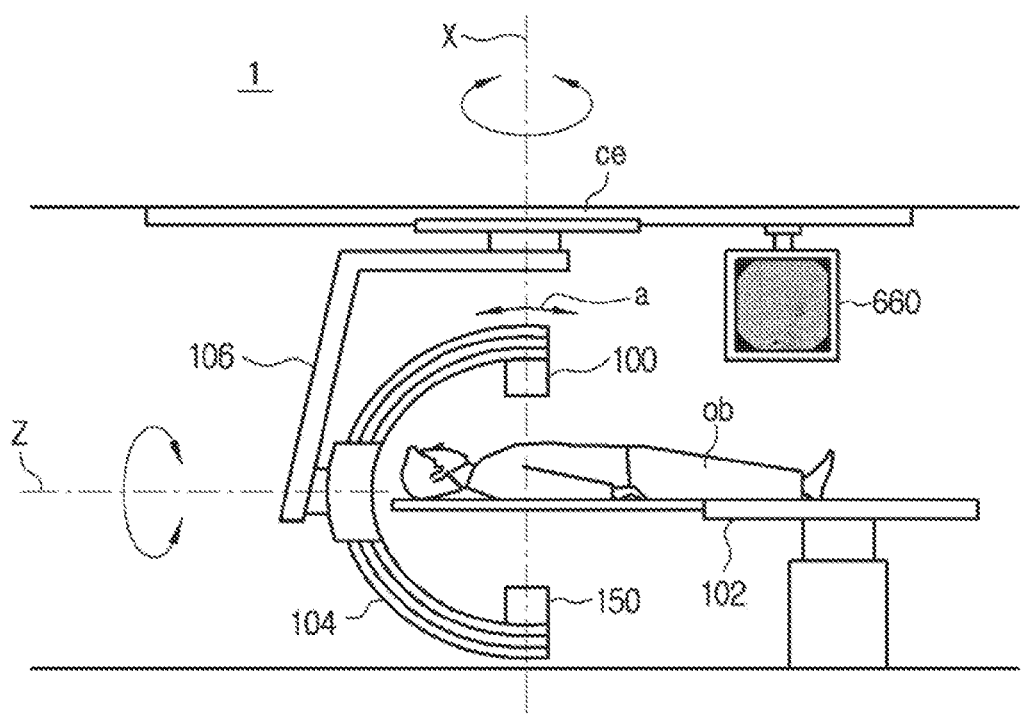
FIG. 1 illustrates an external appearance of an X-ray imaging apparatus according to an exemplary embodiment.

Hereinafter, exemplary embodiments of the present disclosure will be described in detail with reference to the appended drawings such that one of ordinary skill in the art can easily understand and embody the exemplary embodiments. In the following description, well-known functions or constitutions will not be described in detail if the well-known functions or constitutions would unnecessarily obscure the exemplary embodiments of the present disclosure.

Further, terms used in exemplary embodiments as described below are defined in consideration of functions in the exemplary embodiments, and the meanings of the terms may vary depending on a user's or operator's intention or practice. Therefore, the terms used in the exemplary embodiments should be interpreted based on the definition in the specification, and unless specifically defined, the terms are interpreted as common meanings of the terminologies that one of ordinary skill in the art to which the exemplary embodiments pertain understands.

Also, in the following description, aspects described optionally or configurations of exemplary embodiments described optionally must be construed as being able to be freely combined with each other, if not specified otherwise, even if the aspects or configurations are shown as a single integrated configuration in the drawings, unless the combination is clearly a technical contradiction as determined by one of ordinary skill in the art.

Hereinafter, exemplary embodiments of an X-ray imaging apparatus and a control method for the same will be described in detail with reference to the appended drawings.

Hereinafter, an X-ray imaging apparatus according to an exemplary embodiment will be described with reference to FIGS. 1 and 2.

FIG. 1 illustrates an external appearance of an X-ray imaging apparatus according to an exemplary embodiment.

Referring to FIG. 1, an X-ray imaging apparatus 1 may include an X-ray generator 100, and an X-ray detector 150 disposed to face the X-ray generator 100.

The X-ray generator 100 may generate X-rays and irradiate the X-rays onto an object ob, in order to acquire an X-ray image of the object ob.

The X-ray detector 150 may detect the X-rays transmitted through the object ob. Also, the X-ray detector 150 may convert the detected X-rays into X-ray data that is electrical signals, and then convert the X-ray data into image signals, thereby generating an image frame which is an X-ray image of the object ob.

The object ob may be a human's or animal's living body, however, the object ob is not limited to these examples. That is, the object ob may be an anything having an internal structure which can be imaged by the X-ray imaging apparatus 1.

The X-ray imaging apparatus 1 may further include a table 102 to accommodate the object ob. Accordingly, when X-rays are irradiated from the X-ray generator 100, the object ob may be accommodated by the table 102 such that the object ob is placed between the X-ray generator 100 and the X-ray detector 150.

The X-ray generator 100 and the X-ray detector 150 may be respectively positioned at the facing ends of a C-arm 104. The C-arm 104 may be rotatable with respect to a horizontal axis denoted as a z-axis. Also, the C-arm 104 may move in a direction denoted by an arrow a, while making a circular or semicircular trajectory. Also, the C-arm 104 may be connected to a supporting unit 106 mounted on the ceiling ce, and the supporting unit 106 may be rotatable with respect to a vertical axis denoted by an x-axis. Accordingly, by rotating the C-arm 104 and the supporting unit 106, various Regions Of Interest (ROI) of the object ob can be scanned in various directions so that X-ray images about the ROI of the object ob can be acquired with respect to various directions.

An X-ray image of the object ob, acquired by performing predetermined image processing on the electrical signals of the X-rays detected by the X-ray detector 150, may be displayed on a display 660. In FIG. 1, a case in which the display 660 is mounted on the ceiling ce is shown, however, the location of the display 660 is not limited thereto.

Figure 2:
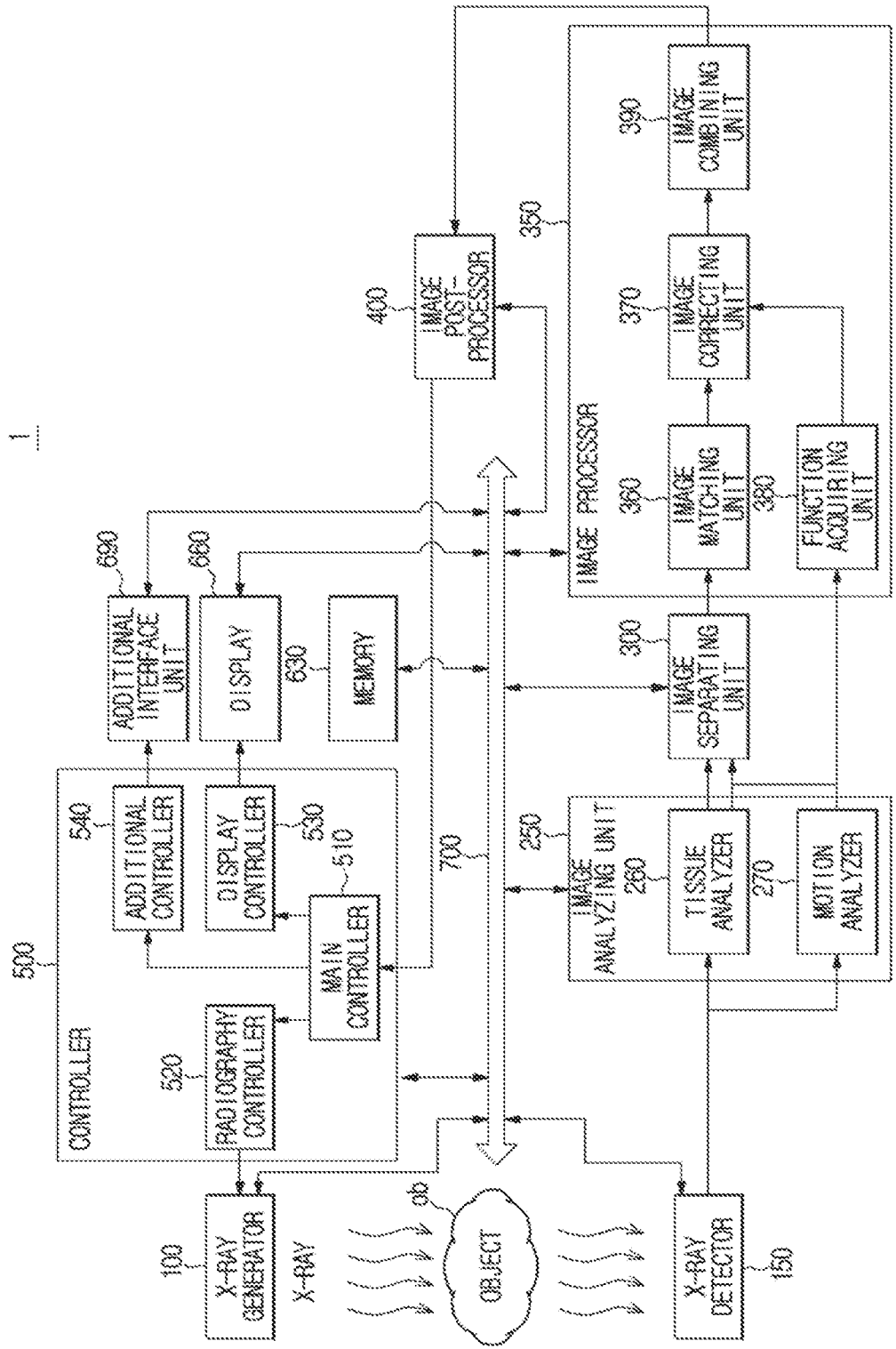
FIG. 2 is a block diagram illustrating a configuration of an X-ray imaging apparatus according to an exemplary embodiment.

Also, the X-ray imaging apparatus 1 may further include an additional interface unit 690 (e.g., "additional interface") (see FIG. 2). The additional interface 690 may include one or more switches, a keyboard, a trackball, or a touch screen, although the additional interface 690 is not limited to one of the above-mentioned devices.

The display 660 may be a Cathode Ray Tube (CRT), a Liquid Crystal Display (LCD), a Light Emitting Diode (LED) display, or an Organic Light Emitting Diode (OLED) display, although the display 660 is not limited to one of the above-mentioned devices.

FIG. 2 is a block diagram illustrating a configuration of the X-ray imaging apparatus 1 according to an exemplary embodiment.

Referring to FIG. 2, the X-ray imaging apparatus 1 may include the X-ray generator 100, the X-ray detector 150, an image analyzing unit 250 (e.g., image analyzer), an image separating unit 300 (e.g., image separator), an image processor 350, an image post-processor 400, a controller 500, a memory 630, the display 660, and the additional interface 690. The above-mentioned components may be connected to each other through a bus 700.

The X-ray generator 100 may generate X-rays, and irradiate the X-rays onto the object ob. The X-ray generator 100 may receive power from a power supply to generate X-rays, wherein the energy of the X-rays can be controlled according to a tube voltage, and the intensity or dose of the X-rays can be controlled according to a tube current or an X-ray exposure time.

The X-ray generator 100 may irradiate monochromatic X-rays, or polychromatic X-rays having a predetermined energy band. When the X-ray generator 100 irradiates polychromatic X-rays, an energy band of X-rays to be irradiated may be defined by upper and lower limits.

The upper limit of the energy band, that is, a maximum energy of X-rays to be irradiated, may be adjusted according to the magnitude of a tube voltage, and the lower limit of the energy band, that is, a minimum energy of X-rays to be irradiated, may be adjusted by a filter included in or provided outside the X-ray generator 100. By filtering out a low energy band of X-rays using the filter, an average energy of X-rays to be irradiated may increase.

The X-ray detector 150 may detect X-rays transmitted through the object ob, convert the X-rays into X-ray data that is electronic signals, and then convert the X-ray data into image signals, thereby generating an image frame. The term "image frame" may refer to an X-ray image detected by the X-ray detector 150 configured with a plurality of pixels.

Generally, the X-ray detector 150 may be classified according to a material configuration of the X-ray detector 150, a method of converting detected X-rays into electrical signals, and a method of acquiring X-ray data. Hereinafter, various methods in which the X-ray detector 150 detects X-rays and converts the detected X-rays into electrical signals to acquire X-ray data will be described.

The X-ray detector 150 is classified into a mono type device or a hybrid type device according to a material configuration of the X-ray detector 150.

If the X-ray detector 150 is a mono type device, a part of detecting X-rays and generating electrical signals, and a part of reading and processing the electrical signals may be semiconductors made of the same material, or may be manufactured by one process. In this case, the X-ray detector 150 may be a Charge Coupled Device (CCD) or a Complementary Metal Oxide Semiconductor (CMOS) which is a light receiving device 160 (see FIG. 6).

If the X-ray detector 150 is a hybrid type device, a part of detecting X-rays and generating electrical signals, and a part of reading and processing the electrical signals may be made of different materials, or may be manufactured by different processes. For example, the X-ray detector 150 may detect X-rays using a photodiode or the light receiving device 160, such as CCD or CdZnTe, and may read and process electrical signals using a CMOS Read Out Integrated Circuit (CMOS ROIC), the X-ray detector may detect X-rays using a strip detector, may read and process electrical signals using CMOS ROIC, and may use an a-Si or a-Se flat panel system.

The X-ray detector 150 may use a direct conversion mode and an indirect conversion mode according to a method of converting X-rays into electrical signals.

In the direct conversion mode, if X-rays are irradiated, electron-hole pairs are temporarily generated in the light receiving device 160, electrons move to an anode 113 (see FIG. 3) and holes move to a cathode 115 (see FIG. 3) by an electric field applied to both terminals of the light receiving device 160, and the X-ray detector 150 converts the movement of the electrons and holes into an electrical signal. The light receiving device 160 may be made of a-Se, CdZnTe, $HgI_2$, or $PbI_2$.

In the indirect conversion mode, a scintillator is provided between the light receiving device 160 and the X-ray generator 100. If X-rays irradiated from the X-ray generator 100 react with the scintillator to emit photons having a wavelength of a visible light region, the light receiving device 160 detects the photons, and converts the photons into an electrical signal. The light receiving device 160 may be made of a-Si, and the scintillator may be a GADOX scintillator of a thin film type, or a CSI (TI) of a micro pillar type or a needle type.

The X-ray detector 150 may use a charge integration mode of storing charges for a predetermined time period and then acquiring a signal from the stored charges, or a photon counting mode of counting the number of photons having energy higher than threshold energy whenever a signal is generated by single X-ray photons, according to a method of acquiring X-ray data.

The image analyzing unit 250 may receive the image frame generated by the X-ray detector 150, and analyze tissues of the object ob included in the image frame and motions of the tissues. The image analyzing unit 250 may include a tissue analyzer 260 and a motion analyzer 270.

The tissue analyzer 260 may determine kinds of the tissues included in the image frame, based on attenuation coefficients depending on changes in energy of bone or soft tissue of the object ob. More specifically, the tissue analyzer 260 may compare energy of X-rays irradiated to the object ob by the X-ray generator 100 to energy of X-rays detected by the X-ray detector 150, calculate a ratio of the detected energy to the irradiated energy, and apply a pre-stored attenuation coefficient for the tissue of the object ob, thereby determining a kind of the tissue displayed in the image frame.

Also, the tissue analyzer 260 may analyze a tissue displayed in a current image frame based on tissue data stored in advance in the memory 630, although the tissue has been not displayed in any one of a plurality of image frames.

The motion analyzer 270 may compare a plurality of image frames to each other to analyze motions of tissues displayed in the plurality of image frames.

More specifically, the motion analyzer 270 may express intensity, illumination, luminance, and luminosity values of individual pixels of each image frame in the form of a matrix, and compare matrices of a plurality of image frame to each other, thereby calculating motion vectors.

Also, the motion analyzer 270 may determine a tissue without motion (e.g., with no motion or with motion less than a threshold amount of motion), whether tissues displayed in an image frame have motion, whether each tissue with motion moves in a straight line or in a curved line, a motion direction of each tissue, and a degree of motion of each tissue.

Also, when the motion analyzer 270 extracts a plurality of tissue images from the plurality of image frames based on the analyzed motions of the tissues, the motion analyzer 270 may decide a number of tissue images to be extracted, and decide criteria of motion between tissue images to be separated. That is, the motion analyzer 270 may decide criteria of motion according to a motion of a tissue that should be corrected, a correction value, and a degree of blur that is displayed in a tissue image. However, various factors other than the above-mentioned factors may be used as criteria of motion between tissue images to be separated.

Also, the motion analyzer 270 may decide the number of groups that are to be classified, based on the analyzed motions of tissues. Also, the motion analyzer 270 may decide a range of motions corresponding to the number of groups decided by the motion analyzer 270 or a predetermined number of groups, and group the analyzed motions into a plurality of groups based on the decided range of motions.

As a method in which the motion analyzer 270 analyzes a motion of each tissue, a block matching algorithm and optical flow may be used.

Details for the block matching algorithm and the optical flow will be described with reference to FIGS. 13 and 14, later.

It is understood that other methods for analyzing motions of tissues included in an image frame may be applied for the motion analyzer 270 to analyze motions of tissues.

The image separating unit 300 may extract a plurality of tissue images from the image frame, according to the kinds of the tissues displayed in the image frame or the motions of the tissues, analyzed by the image analyzing unit 250.

According to an exemplary embodiment, the tissue images are images acquired by separating the tissues displayed in the image frame according to the motions of the tissues. More specifically, the image frame overlaps target regions that exist in different layers of the object ob so that the target regions existing in the different layers are shown as if the target regions exist in the same layer. That is, a tissue image is obtained by extracting an image in which the corresponding tissue is displayed, from the image frame, after classifying target regions shown to exist in the same layer although the target regions exist in substantially different layers, into a plurality of tissues, according to the motions of tissues.

Figure 12:
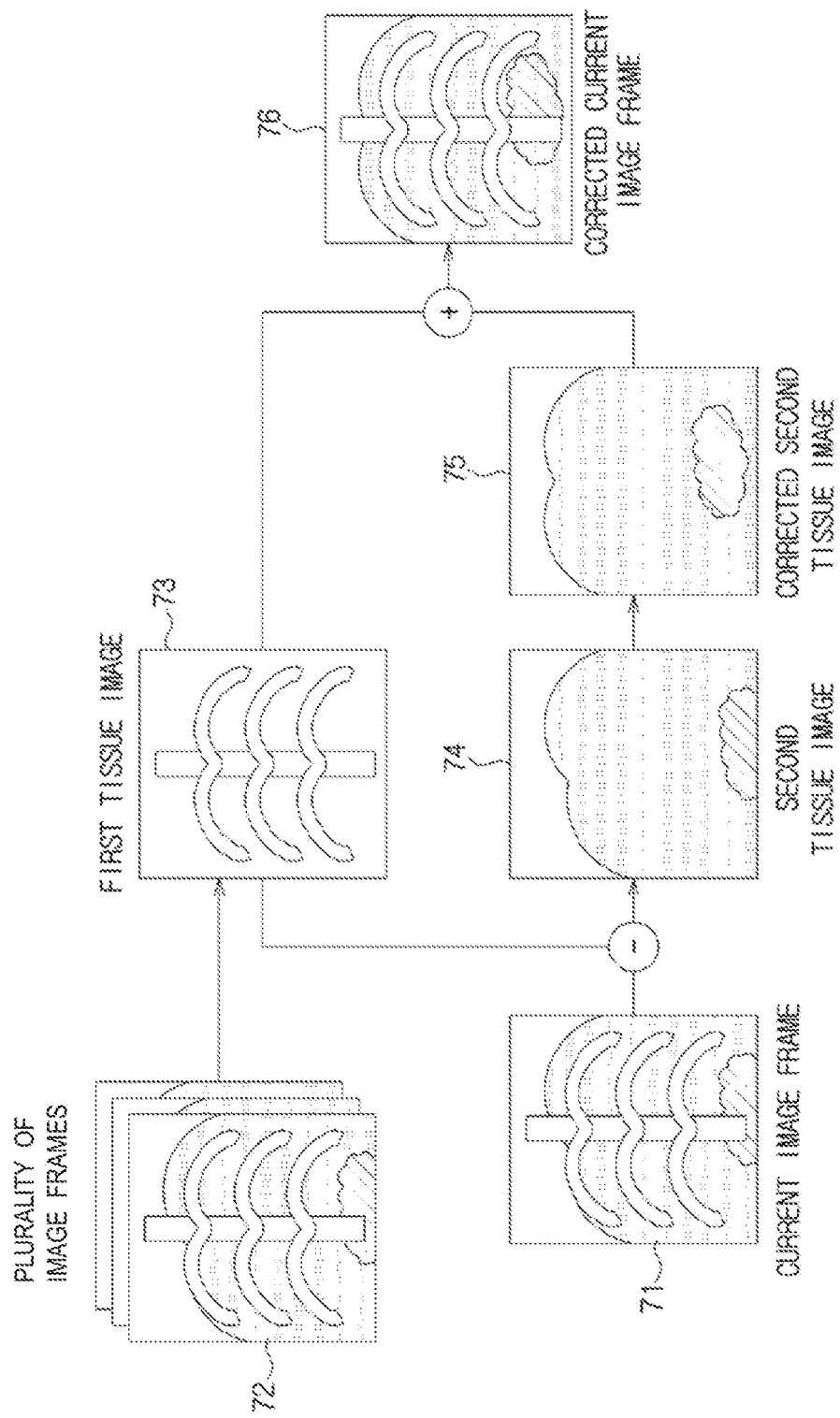
FIG. 12 is a view for describing the concept of a method of separating, correcting, and combining frame images in an X-ray imaging apparatus, according to an exemplary embodiment.

For example, as shown in FIG. 12, it is assumed that the chest of an object ob has been scanned, wherein bone tissues, such as spine and ribs, have no motion, and soft tissues such as organs have motion. In this case, the image separating unit 300 may extract bone tissue images and soft tissue images from a plurality of image frames.

Also, the image separating unit 300 may display tissues grouped into the same group through tissue motion analysis by the image analyzing unit 250, in a tissue image.

For example, as shown in FIG. 12, the image analyzing unit 250 may designate bone tissues without motion as a first group, and designate a first soft tissue such as the skin of the chest and a second soft tissue such as internal organs, as a second group having similar motions. Thereafter, the image separating unit 300 may extract a tissue image for bone tissue, corresponding to the first group, and a tissue image for first and second soft tissues, corresponding to the second group.

Also, the number of tissue images that are extracted by the image separating unit 300 may be limited by the number of image frames generated by the X-ray detector 150. More specifically, the number of tissue images that are extracted by the image separating unit 300 may be equal to or less than the number of image frames generated by the X-ray detector 150.

For example, as shown in FIG. 12, in order to extract two tissue images, the number of image frames that are generated by the X-ray detector 150 may be two or more.

Also, the number of tissue images that are extracted by the image separating unit 300 may be decided based on various criteria, such as a setting value set when the X-ray imaging apparatus 1 is manufactured, motions of tissues of a currently photographed object ob, the number of acquired image frames, and the number of tissue images input by a user. However, the number of tissue images that are extracted by the image separating unit 300 may be decided by other types of variables as well.

The image separating unit 300 may select an image frame from among the plurality of image frames to extract a tissue image without motion from the selected image frame, and select another image frame from among the plurality of image frames to extract a tissue image with motion from the selected image frame. For example, the image separating unit 300 may extract a first tissue image from a first image frame, a second tissue image from a second image frame, and an n-th tissue image from an n-th image frame.

Also, the image separating unit 300 may select an image frame from among the plurality of image frames to extract a tissue image without motion from the selected image frame, and then remove components of the extracted tissue image without motion from another image frame selected from among the plurality of image frames to extract a tissue image with motion. For example, the image separating unit 300 may extract a first tissue image which is a tissue image without motion, from a first image frame, and remove components of the first tissue image from a second image frame to extract a second tissue image which is a tissue image with motion.

The image processor 350 may correct the plurality of tissue images extracted by the image separating unit 300, based on the kinds of the tissues of the object ob and the motions of the tissues, analyzed by the image analyzing unit 250, and combine the corrected tissue images to generate a corrected image frame. The image processor 350 may include an image matching unit 360 (e.g., image matcher), a function acquiring unit 380 (e.g., function acquirer), an image correcting unit 370 (e.g., image corrector), and an image combining unit 390 (e.g., image combiner).

The image matching unit 360 may match the plurality of tissue images. Matching is a processing method of modifying different images so that the different images can be expressed on a coordinate system. The image matching unit 360 may match the plurality of tissue images, for example, the first tissue image and the second tissue image, as shown in FIG. 12. The imaging matching unit 360 may match a plurality of X-ray images, for example, the first tissue image and the second tissue image using an image as a reference image, for example, using the first tissue image as a reference image.

The function acquiring unit 380 may calculate a function for correcting a motion of each tissue based on the motions of the tissues analyzed by the image analyzing unit 250. More specifically, the function acquiring unit 380 may calculate a motion transform matrix for moving a tissue moved according to the motion of the tissue to an original location of the tissue or to a desired location. For example, as shown in FIG. 13, the function acquiring unit 380 may calculate an identity matrix that is to be applied to a first tissue without motion, and a motion transform matrix that is to be applied to a second tissue with motion. Also, the function acquiring unit 380 may convert the motion vectors calculated by the image analyzing unit 250 into a motion transform matrix.

Also, the function acquiring unit 380 may calculate a function for correction for each group, so that a function is applied to the same group into which tissues having similar motions have been grouped by the image analyzing unit 250.

Also, the function acquiring unit 380 may estimate a location of a tissue with motion before the motion occurs, a location of the tissue after the motion occurs, and a location of the tissue when the tissue is being photographed, based on the kinds of the tissues and the motions of the tissues analyzed by the image analyzing unit 250, and calculate a function for correcting the motion of the tissue based on the estimated locations of the tissue.

The image correcting unit 370 may apply the motion transform function calculated by the function acquiring unit 380 to the plurality of tissue images to correct the plurality of tissue images. For example, as shown in FIG. 13, the image correcting unit 370 may apply the identity matrix to a first tissue image without motion to fix the first tissue at a location I22, and apply the motion transform matrix to a second tissue image with motion to locate the second tissue at a location I23.

Also, the image correcting unit 370 may perform group-based correction, wherein tissues having similar motions have been grouped into the same group, and correct tissue images corresponding to the same group using the same correction value.

The image combining unit 390 may combine the plurality of tissue images corrected by the image correcting unit 370 to generate a corrected image frame. For example, the image combining unit 390 may combine the first tissue image with the second tissue image to generate a corrected current image frame, as shown in FIG. 12.

Also, the image combining unit 390 may compare the plurality of tissue images to each other for each area to select or extract areas with minimum noise from the plurality of tissue images, and combine the areas with minimum noise. Alternatively, the image combining unit 390 may compare the plurality of tissue images to each other for each area to select or extract areas with smaller noise from the plurality of tissue images, allocate greater weights to the areas with smaller noise, and then combine the areas with smaller noise. At this time, the plurality of tissue images may be compared in units of a pixel, in units of a predetermined area that is larger than a pixel, or in units of an area that is set according to the properties of the object ob.

The image post-processor 400 may adjust the brightness, contrast, or sharpness of the entire or a part of an image frame output from the image processor 350 to thereby correct the image frame. Also, the image post-processor 400 may apply various image post-processing methods to the image frame in order to post-process the image frame. Further, the image post-processor 400 may overlap a plurality of image frames to generate an overlapped image frame, or the image post-processor 400 may produce a 3-Dimensional (3D) stereo image frame using a plurality of image frames. The post-processed image frame may be stored in the memory 630, such as a semiconductor storage or a magnetic disc storage, or transferred to the display 660 or the additional interface 690 so that the post-processed image frame is displayed for a user.

The controller 500 may transfer control signals to components for performing predetermined operations in order to perform operations of the X-ray imaging apparatus 1 according to a command input by a user. Also, the controller 500 may control overall operations of the X-ray imaging apparatus 1, control signal flows of the internal components of the X-ray imaging apparatus 1, and process data. Also, the controller 500 may transfer power supplied from a power source to the internal components of the X-ray imaging apparatus 1. Also, the controller 500 may control the X-ray generator 100 to adjust a dose and intensity of X-rays that are to be irradiated to the object ob, and an irradiation direction of X-rays, and control the display 660 to display a corrected image frame.

The controller 500 may function as a Central Processing Unit (CPU) which may be a microprocessor. The microprocessor is a processing unit in which an Arithmetic Logic Unit (ALU), a register, a program counter, an instruction decoder, a control circuit, etc., are packaged in at least one silicon chip.

The microprocessor may include a Graphic Processing Unit (GPU) for graphic processing of images or video. The microprocessor may be implemented in the form of a System On Chip (SoC) including a core and a GPU. The microprocessor may include a single core, a dual core, a triple core, a quad core, and a multiple core.

Also, the controller 500 may include a graphic processing board including a GPU, RAM, or ROM, which is mounted on a separate circuit substrate electrically connected to the microprocessor.

Also, the controller 500 may include a main controller 510, a radiography controller 520, a display controller 530, and an additional controller 540.

The main controller 510 may transfer overall control signals for operations of the X-ray imaging apparatus 1 to components that are driven, the radiography controller 520, the display controller 530, and the additional controller 540.

More specifically, the main controller 510 may decide the number of tissue images that are to be extracted by the image separating unit 300 and the kinds of tissues that are to be extracted by the image separating unit 300, based on analysis signals from the image analyzing unit 250, obtained by analyzing an image frame generated by the X-ray detector 150, and control the image separating unit 300 to extract tissue images from the image frame. Also, the main controller 510 may calculate a correction value which the image processor 350 is set to apply to each of the extracted tissue images, based on a motion of the tissue image, and control the image processor 350 to apply different corrections to the respective tissue images. Also, the main controller 510 may control the image processor 350 to combine the plurality of corrected tissue images to generate a corrected image frame. Also, the main controller 510 may receive the corrected image frame, and transfer image signals corresponding to the corrected image frame to the display controller 530 so that the display controller 530 displays the image frame.

Also, the main controller 510 may repeatedly perform operations of comparing a plurality of image frames to each other to extract, correct, and combine a plurality of tissue images, and then comparing, instead of comparing a plurality of image frames to each other, the corrected image frame to a current image frame to extract, correct, and combine a plurality of tissue images. Also, the main controller 510 may perform operations of comparing the corrected image frame to the current image frame to extract, correct, and combine the plurality of tissue images, until the corrected image frame converges on the current image frame.

Also, the main controller 510 may perform optimization in order to obtain maximum efficiency within a processing speed limit of the controller 500.

More specifically, the main controller 510 may control the image separating unit 300 and the image processor 350 to use different methods of analyzing motions, wherein the image separating unit 300 analyzes motions to extract tissue images, and the image processor 350 analyzes motions to correct tissue images. For example, a method in which the image separating unit 300 analyzes motions to extract tissue images may be simpler than a method in which the image processor 350 analyzes motions to correct tissue images. In this case, the main controller 519 may control the image separating unit 300 to use a method requiring a smaller amount of computation while having low accuracy to analyze motions for extracting tissue images, and may control the image processor 350 to use a method having high accuracy while requiring a greater amount of computation to analyze motion for correcting tissue images.

Also, the main controller 510 may perform operations of extracting tissue images without motion, correcting only tissue images with motion without correcting the tissue images without motion, and then combining the tissue images, several times, thereby reducing the throughput of the main controller 510.

The radiography controller 520 may decide energy of X-rays that are to be irradiated from the X-ray generator 100 to the object ob, based on the kinds of the tissues and the motions of the tissues analyzed by the image analyzing unit 250, and control the X-ray generator 100 to generate X-rays that are to be irradiated to the object ob based on the decided energy of X-rays, and irradiate the X-rays to the object ob. Also, the radiography controller 520 may control radiography conditions, such as a tube voltage and tube current to be supplied to the X-ray generator 100 and an X-ray exposure time, according to the properties of the object ob. Also, the radiography controller 520 may determine whether to generate single-energy X-ray images or multi-energy X-ray images.

The display controller 530 may receive a control signal and an image signal from the main controller 510, and control the display 660 to display the corrected image frame.

The additional controller 540 may control the operations of the remaining components of the X-ray imaging apparatus 1, except for components that are controlled by the radiography controller 520 and the display controller 530. For example, the additional controller 540 may transfer a user input signal received through the additional interface 690, such as one or more switches, a trackball, or a touch screen, to the main controller 510, or the additional controller 540 may control another output unit except for the display 660 to display the operation of the X-ray imaging apparatus 1 based on a control signal from the main controller 510 so that the user can recognize the operation.

The memory 630 may store image frame signals generated by the X-ray detector 150, information about the kinds and motions of tissues displayed in image frames, analyzed by the image analyzing unit 250, tissue image signals extracted by the image separating unit 300, correction functions calculated by the function acquiring unit 380, and corrected image frame signals combined by the image combiner 390. Also, the memory 630 may store tissue data in order to enable the image analyzing unit 250 to analyze a tissue displayed in a current image frame, the tissue not being displayed in the plurality of image frames.

The memory 630 may include Read Only Memory (ROM), Random Access Memory (RAM), a magnetic disc storage unit, a non-volatile memory such as a flash memory, or another non-volatile semiconductor memory device.

For example, the memory 630 may use, as a semiconductor memory device, a Secure Digital (SD) memory card, a Secure Digital High Capacity (SDHC) memory card, a mini SD memory card, a mini SDHC memory care, a Trans Flash (TF) memory card, a micro SD memory card, a micro SDHC memory card, a memory stick, Compact Flash (CF), a Multi-Media Card (MMC), MMC micro, or an eXtreme Digital (XD) card.

Also, the memory 630 may include a network-attached storage device that is accessed through a network.

The display 660 may display a corrected image frame obtained by combining tissue images corrected by the image processor 350 so that a user can perform diagnosis through image analysis.

Also, the display 660 may be a CRT, an LCD, an LED display, or an OLED display, although the display 660 is not limited to one of the above-mentioned devices.

The additional interface 690 may include an input device, such as one or more switches, a keyboard, a trackball, or a touch screen, so that the user can control the X-ray imaging apparatus 1, and an output device, such as a speaker or an vibrator, so that the user can recognize a current operation of the X-ray imaging apparatus 1.

Hereinafter, the X-ray generator 100 according to an exemplary embodiment will be described with reference to FIGS. 3, 4, and 5.

Figure 3:
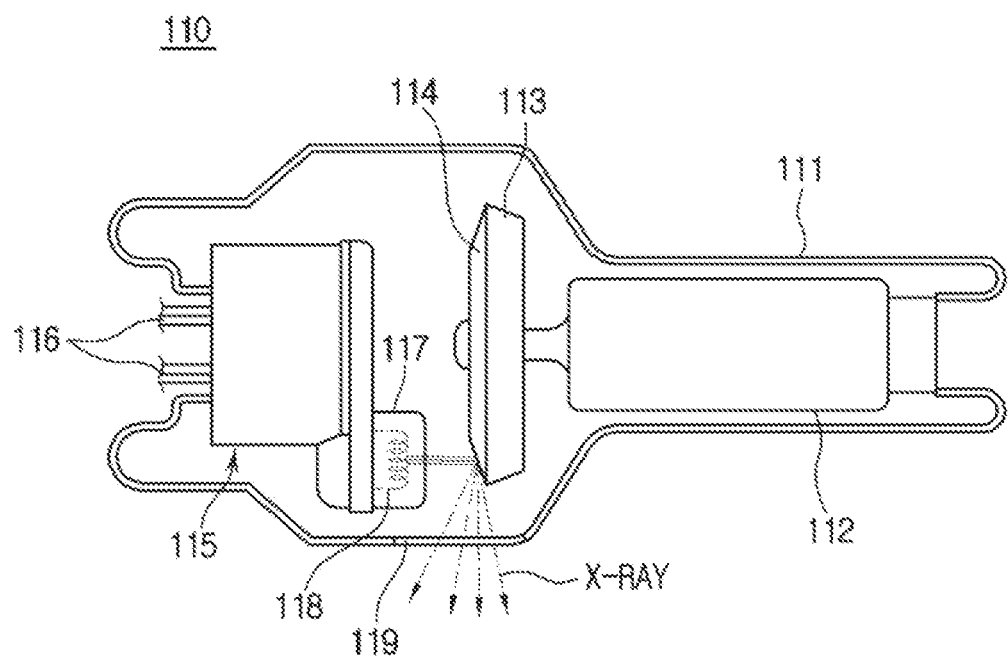
FIG. 3 is a cross-sectional view of an X-ray generator according to an exemplary embodiment.

FIG. 3 is a cross-sectional view of the X-ray generator 100 according to an exemplary embodiment.

Referring to FIG. 3, the X-ray generator 100 may include an X-ray tube 110 to generate X-rays. The X-ray tube 110 may be also called an X-ray tube head or an X-ray tube assembly. The X-ray tube 110 may be embodied as a two-electrode vacuum tube 111 including an anode 113 and a cathode 115. The body of the two-electrode vacuum tube may be a glass tube made of silica (hard) glass or the like.

The cathode 115 may include a filament 118 and a focusing electrode 117 for focusing electrons, and the focusing electrode 117 is also called a focusing cup. The inside of a glass tube 111 is evacuated to a high vacuum state of about 10 mmHg, and the filament 118 of the cathode 115 is heated to a high temperature, thereby generating thermoelectrons. The filament 118 may be a tungsten filament, and the filament 118 may be heated by applying current to electrical leads 116 connected to the filament 118.

The anode 113 may be made of copper, and a target material 114 is applied on the surface of the anode 113 facing the cathode 115, wherein the target material 114 may be a high-resistance material, e.g., Cr, Fe, Co, Ni, W, or Mo. The higher the melting point of the target material 114, the smaller the focal spot size.

When a high voltage is applied between the cathode 115 and the anode 113, thermoelectrons are accelerated and collide with the target material 114 of the anode 113, thereby generating X-rays. The X-rays are irradiated to the outside through a window 119. The window 119 may be a Beryllium (Be) thin film. Also, a filter (not shown) for filtering a specific energy band of X-rays may be provided on the front or rear side of the window 119.

The target material 114 may be rotated by a rotor 112. When the target material 114 rotates, the heat accumulation rate may increase 10 times per unit area and the focal spot size may be reduced, compared to when the target material 114 is fixed.

The voltage that is applied between the cathode 115 and the anode 113 of the X-ray tube 111 is called a tube voltage. The magnitude of a tube voltage may be expressed as a crest value (kVp). When the tube voltage increases, the velocity of thermoelectrons increases accordingly. Then, energy (energy of photons) of X-rays that are generated when the thermoelectrons collide with the target material 114 also increases. Current flowing through the X-ray tube 111 is called tube current, and can be expressed as an average value (mA). When tube current increases, a dose of X-rays (that is, the number of X-ray photons) increases.

In summary, energy of X-rays can be controlled by adjusting a tube voltage. Also, a dose or intensity of X-rays can be controlled by adjusting tube current and an X-ray exposure time. Accordingly, it is possible to control the energy and intensity of X-rays to be irradiated according to the kind or properties of an object ob.

When X-rays to be irradiated have a predetermined energy band, the predetermined energy band may be defined by upper and lower limits. The upper limit of the predetermined energy band, that is, a maximum energy of X-rays to be irradiated, may be adjusted by the magnitude of a tube voltage, and the lower limit of the predetermined energy band, that is, minimum energy of X-rays to be irradiated, may be adjusted by a filter. By filtering out a low energy band of X-rays using the filter, an average energy of X-rays to be irradiated may increase.

Although not shown in FIG. 3, the X-ray generator 100 may further include a collimator in front of the window 119. The collimator may function to adjust an irradiation range of X-rays that are irradiated from the X-ray tube 110, and to reduce scattering of X-rays.

Figure 4:
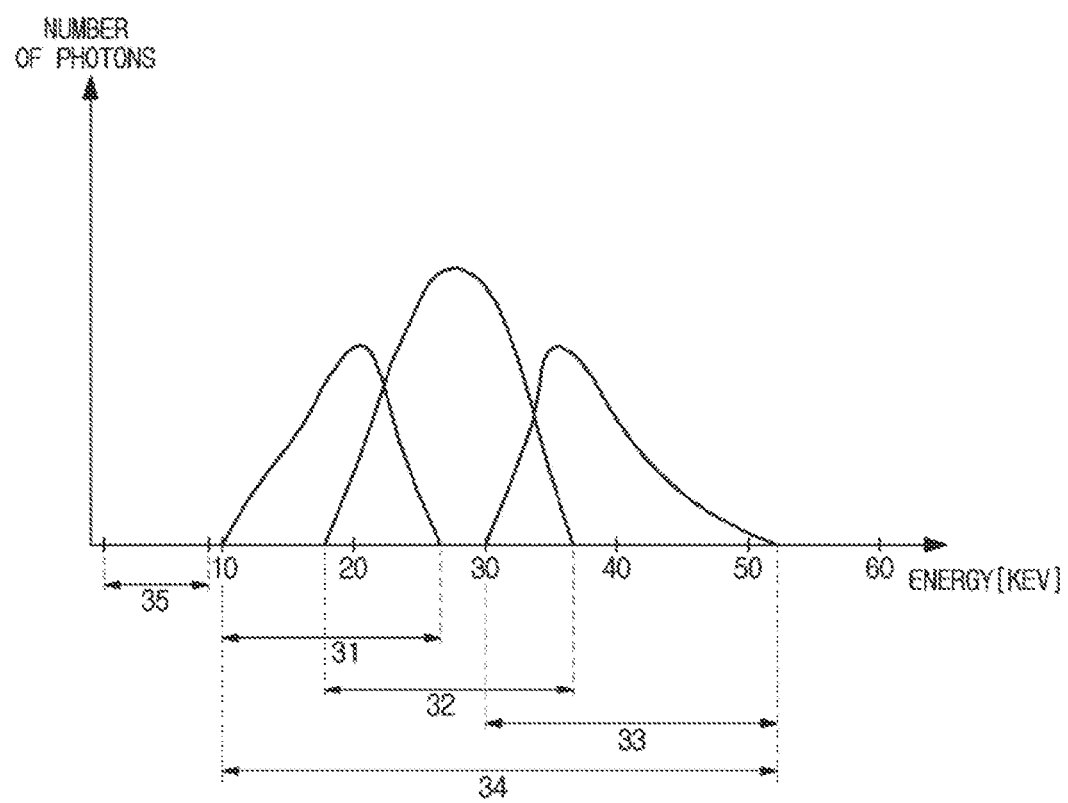
FIG. 4 is a graph showing an example of energy spectrums of X-rays having different energy bands, according to an exemplary embodiment.

FIG. 4 is a graph showing energy spectrums of X-rays having different energy bands, according to an exemplary embodiment.

A plurality of X-rays having different energy bands, which are generated by the X-ray generator 100, may include X-rays having a first energy band 31, X-rays having a second energy band 32, and X-rays having a third energy band 33. Generally, an energy band refers to a range of energy that is defined by the upper and lower limits of energy of X-rays, and an energy spectrum is expressed in the form of a graph that represents a change in intensity of X-rays with respect to a change of energy. The intensity of X-rays is the number of photons of the X-rays, and the energy is expressed in units of Kilo electron volts (Kev).

Figure 5:
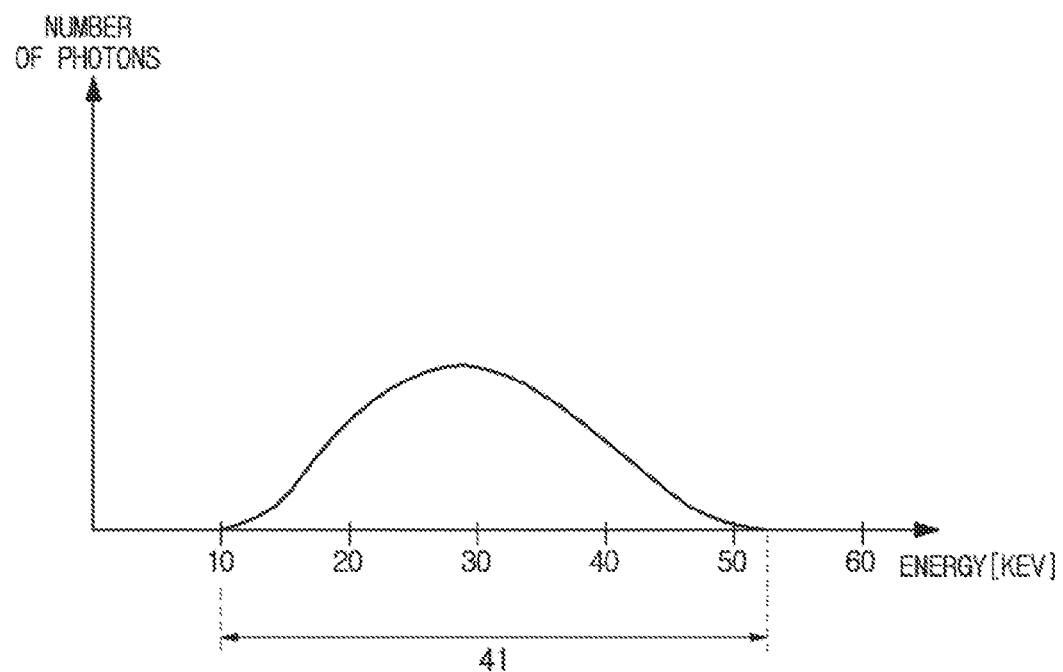
FIG. 5 is a graph showing an example of an energy spectrum of X-rays generated by an X-ray generator according to an exemplary embodiment.

FIG. 5 is a graph showing an example of an energy spectrum of X-rays generated by the X-ray generator 100 according to an exemplary embodiment.

The X-ray generator 100 may generate X-rays of a single-energy band. The X-rays generated by the X-ray generator 100 are source X-rays, which are different from X-rays of different energy bands as described above.

In other words, the X-ray generator 100 may generate source X-rays having a single-energy band 41. The single-energy band 41 may be a wide energy band ranging from 10 Kev to 53 Kev. Also, as described above, the intensity of X-rays is the number of photons of the X-rays, and the energy is expressed as Kilo electron volt (Kev).

Hereinafter, the X-ray detector 150 according to an exemplary embodiment will be described with reference to FIGS. 6 to 9.

Figure 6:
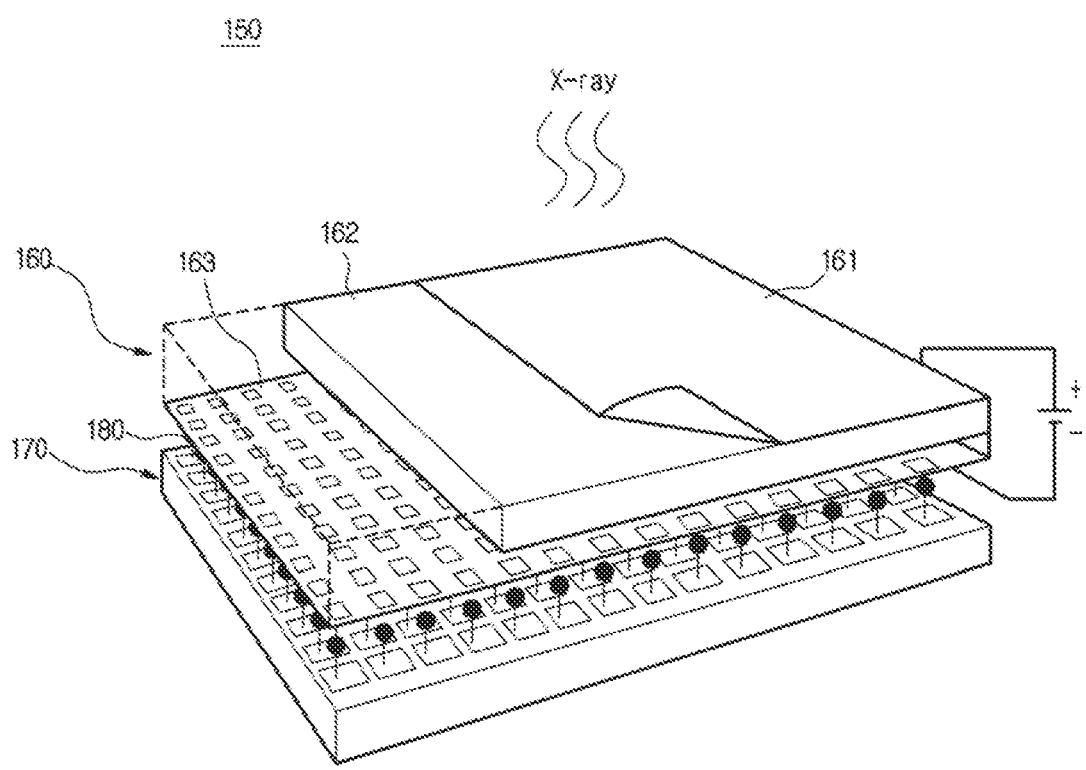
FIG. 6 illustrates an external appearance of an X-ray detector according to an exemplary embodiment.
Figure 7:
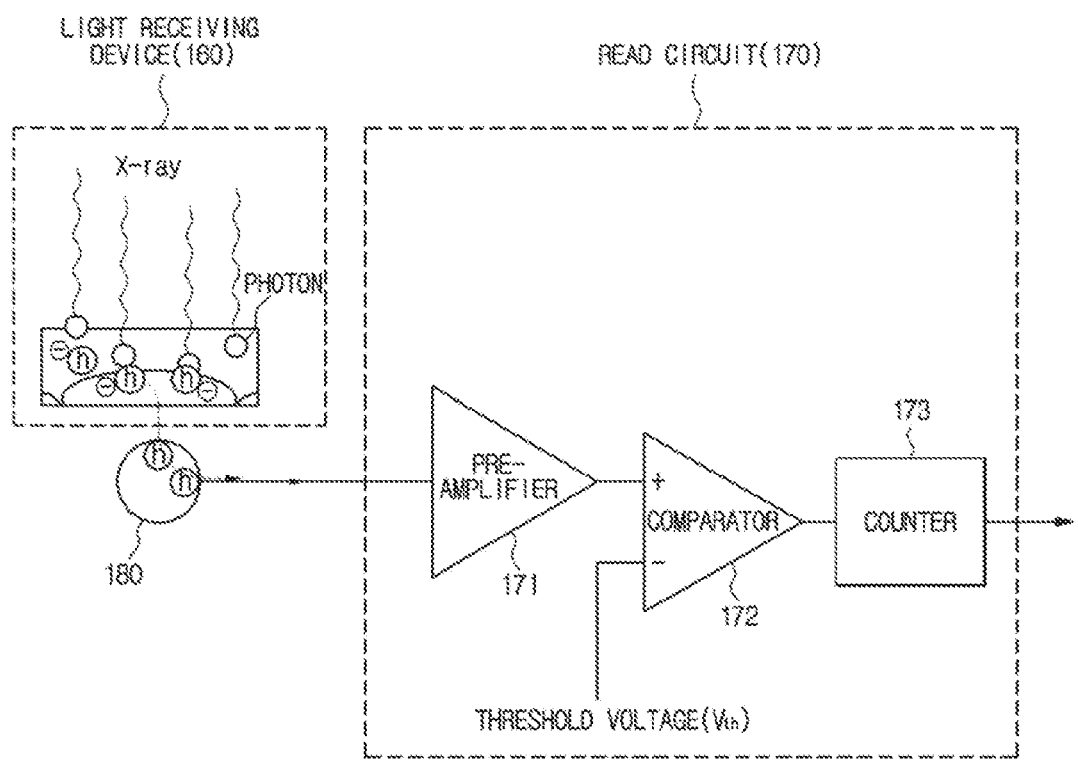
FIG. 7 illustrates a structure of a pixel area of an X-ray detector according to an exemplary embodiment.

FIG. 6 illustrates an external appearance of the X-ray detector 150 according to an exemplary embodiment, and FIG. 7 illustrates a structure of a pixel area of the X-ray detector 150 according to an exemplary embodiment.

Referring to FIG. 6, the X-ray detector 150 may include a light receiving device 160 to detect X-rays and convert the X-rays into electrical signals, and a read circuit 170 to read out the electrical signals.

The read circuit 170 may have a 2D pixel array structure including a plurality of pixels.

The light receiving device 160 may be made of a single crystal semiconductor material in order to ensure high resolution, high response speed, and a high dynamic area even under conditions of low energy and a small dose of X-rays. The single crystal semiconductor material may be Ge, CdTe, CdZnTe, or GaAs.

The light receiving device 160 may be in the form of a PIN photodiode. The PIN photodiode may be fabricated by bonding a p-type layer 163 on which P-type semiconductors are arranged in a 2D pixel array structure on the lower surface of a n-type semiconductor substrate 162 having high resistance. The read circuit 170, which is fabricated according to a Complementary Metal Oxide Semiconductor (CMOS) process, may be coupled with the light receiving device 160 in units of pixels. The CMOS read circuit 170 and the light receiving device 160 may be coupled by a Flip-Chip Bonding (FCB) method. More specifically, the CMOS read circuit 170 and the light receiving device 160 may be coupled by forming bumps 180 with PbSn, In, or the like, reflowing, applying heat, and then compressing. However, the structure of the X-ray detector 150 is not limited to the example described above.

As illustrated in FIG. 7, when X-ray photons are incident to the light receiving device 160, electrons that have been in a valence band receive the energy of the photons so that the total energy of the electrons exceeds a bandgap energy difference to excite the electrons to a conduction band. Thereby, electron-hole pairs are created in a depletion region.

When metal electrodes are respectively formed on the p-type layer 163 and the n-type substrate 162 of the light receiving device 160, and a reversed bias voltage is applied between the p-type layer 163 and the n-type substrate 162, the electrons in the electron-hole pairs created in the depletion region move to the n-type region, and the holes move to the p-type region. The holes moved to the p-type region are input to the read circuit 170 through the bumps 180 so that the read circuit 170 can read electrical signals generated by the photons. However, the electrons may be input to the read circuit 170 to generate electrical signals according to the structure of the light receiving device 160, an applied voltage, etc.

The read circuit 170 may have a 2D pixel array structure corresponding to the p-type semiconductors of the light receiving device 160, and read out an electrical signal in a unit of a pixel. If charges are input from the light receiving device 160 to the read circuit 170 through the bumps 180, a pre-amplifier 171 of the read circuit 170 charges an input charge generated from a photon, and outputs a voltage signal corresponding to the input charge.

The voltage signal output from the pre-amplifier 171 is transferred to a comparator 172. The comparator 172 compares the voltage signal to a threshold voltage that can be controlled by an external device, and outputs a pulse signal of "1" or "0" according to the result of the comparison to a counter 173. The counter 173 counts the number of "1", and outputs the count value as X-ray data which is digital data. Then, X-ray data corresponding to individual pixels may be combined to generate an X-ray image of the object ob.

Here, the threshold voltage corresponds to threshold energy E, and in order to count the number of photons having higher energy than the threshold energy E, a threshold voltage corresponding to the threshold energy E is input to the comparator 172. The reason that a threshold energy E can correspond to a threshold voltage is because the magnitude of an electrical signal (a voltage) that is generated by the light receiving device 160 depends on the energy of photons. A threshold voltage corresponding to desired threshold energy can be calculated using a relationship between energy of photons and a voltage to be generated. In an exemplary embodiment which will be described below, inputting threshold energy to the X-ray detector 150 may refer to the same process as inputting a threshold voltage corresponding to threshold energy.

Figure 8:
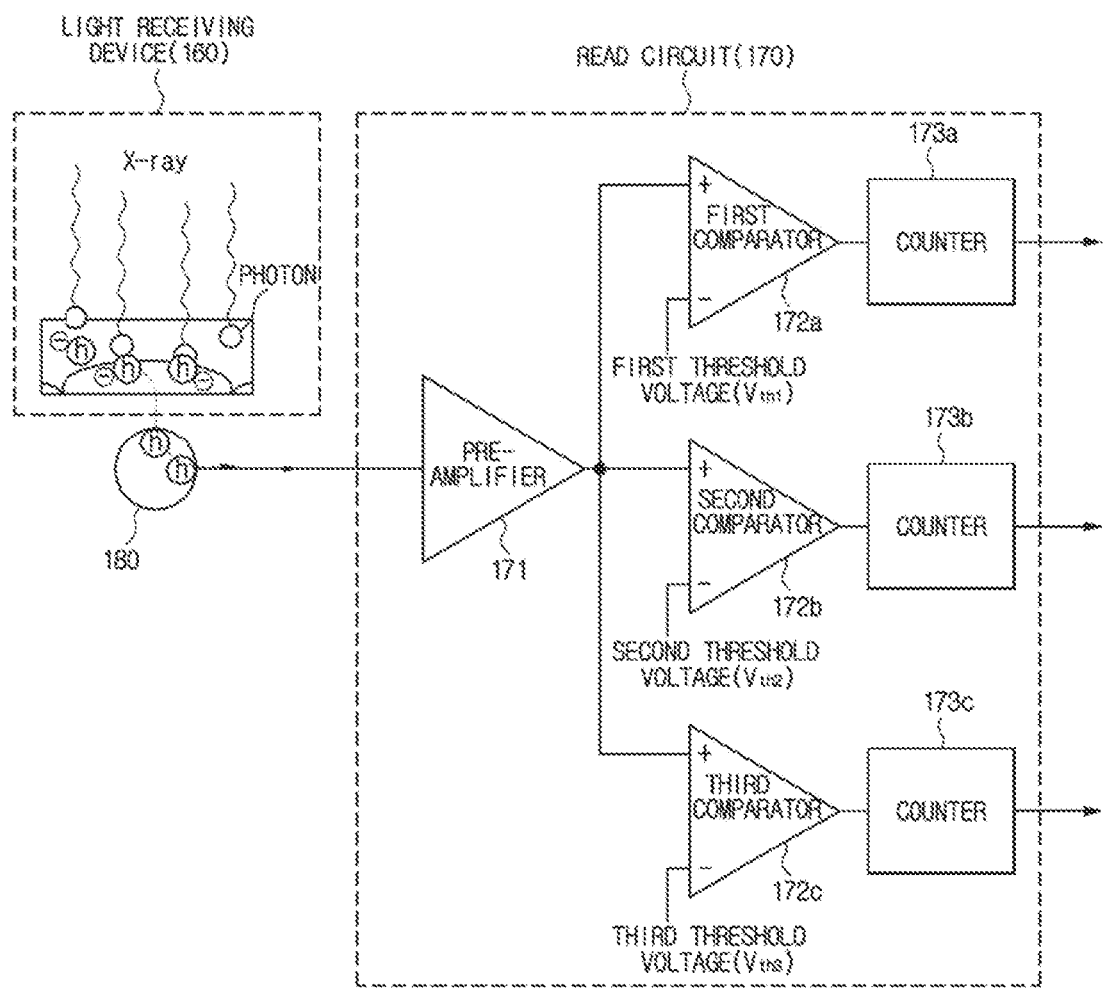
FIG. 8 illustrates a structure of a pixel area of an X-ray detector capable of separating X-rays according to a plurality of different energy bands, according to an exemplary embodiment.

FIG. 8 illustrates a structure of a pixel area of the X-ray detector 150 capable of separating X-rays according to a plurality of different energy bands, according to an exemplary embodiment.

In order to enhance contrast between internal tissues of an object ob, a plurality of X-ray images of a plurality of different energy bands may be acquired to generate a multi-energy X-ray image. In order to acquire a plurality of X-ray images of a plurality of different energy bands, X-rays having different energy bands may be irradiated several times. However, since the X-ray detector 150 (see FIG. 6) of the X-ray imaging apparatus 1 (see FIGS. 1 and 2) may be implemented as a photoconductive decay (PCD) type apparatus, the X-ray generator 100 may irradiate X-rays one time, and the X-ray detector 150 may divide detected X-rays according to a plurality of energy bands.

To do this, as illustrated in FIG. 8, a plurality of comparators (that is, first, second, and third comparators 172a, 172b, and 172c) and a plurality of counters (that is, first, second, and third counters 173a, 173b, and 173c) may be provided to count the number of photons for each energy band. In FIG. 8, an example in which three comparators are provided is shown, however, a different number of comparators may be provided according to the number of energy bands to be divided.

Referring to FIG. 8, when an electron or a hole generated by a single photon is input to the pre-amplifier 171 and then output as a voltage signal, the voltage signal is input to the three comparators 172a, 172b, and 172c. Then, first, second, and third threshold voltages $V_{th1}$, $V_{th2}$, and $V_{th3}$ are applied to the respective comparators 172a, 172b, and 172c. The first comparator 172a compares the voltage signal to the first threshold voltage $V_{th1}$, and the first counter 173a counts the number of photons that have generated a higher voltage than the first threshold voltage $V_{th1}$. In the same way, the second counter 173b counts the number of photons that have generated a higher voltage than the second threshold voltage $V_{th2}$, and the third counter 173c counts the number of photons that have generated a higher voltage than the third threshold voltage $V_{th3}$.

Figure 9:
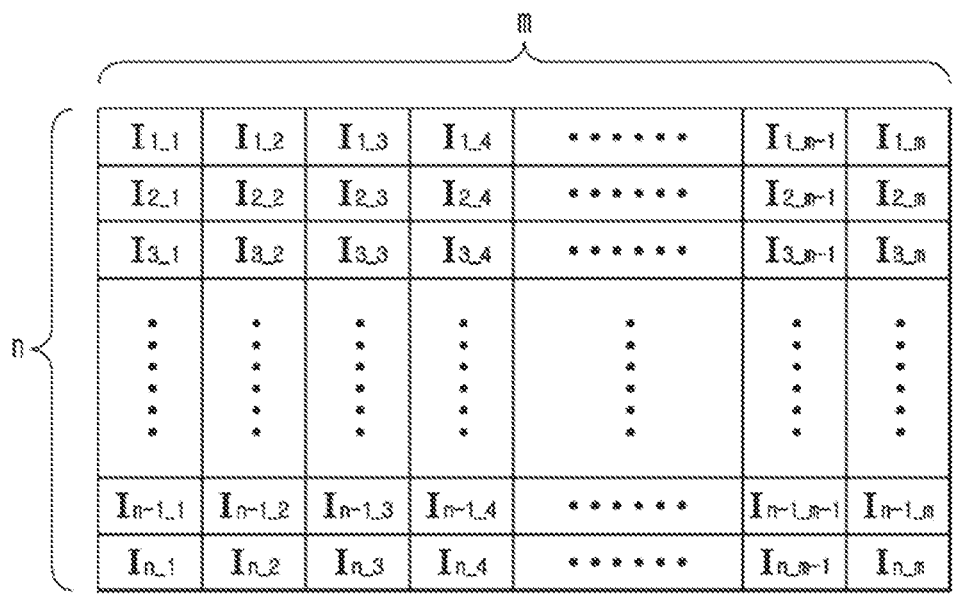
FIG. 9 shows an intensity map for individual pixels of an X-ray detector according to an exemplary embodiment.

FIG. 9 shows an intensity map for individual pixels of the X-ray detector 150 according to an exemplary embodiment.

As described above, the X-ray detector 150 may count the number of photons of each pixel, and then map an intensity value corresponding to the number of photons to the pixel, as shown in FIG. 9.

More specifically, if the X-ray detector 150 is configured with m×n pixels, intensity values of I1_1 to In_m may be extracted for the individual pixels, and mapped to the corresponding pixels.

In FIG. 9, an example in which an intensity value corresponding to an energy value is mapped to each pixel is shown. However, in the case where the X-ray imaging apparatus 1 divides detected X-rays according to a plurality of energy bands, as shown in FIG. 8, it is also possible to map a plurality of intensity values corresponding to a plurality of energy values to each pixel.

Hereinafter, a method of analyzing and detecting internal tissues in an object in an X-ray imaging apparatus, according to an exemplary embodiment, will be described with reference to FIGS. 10 and 11.

Figure 10:
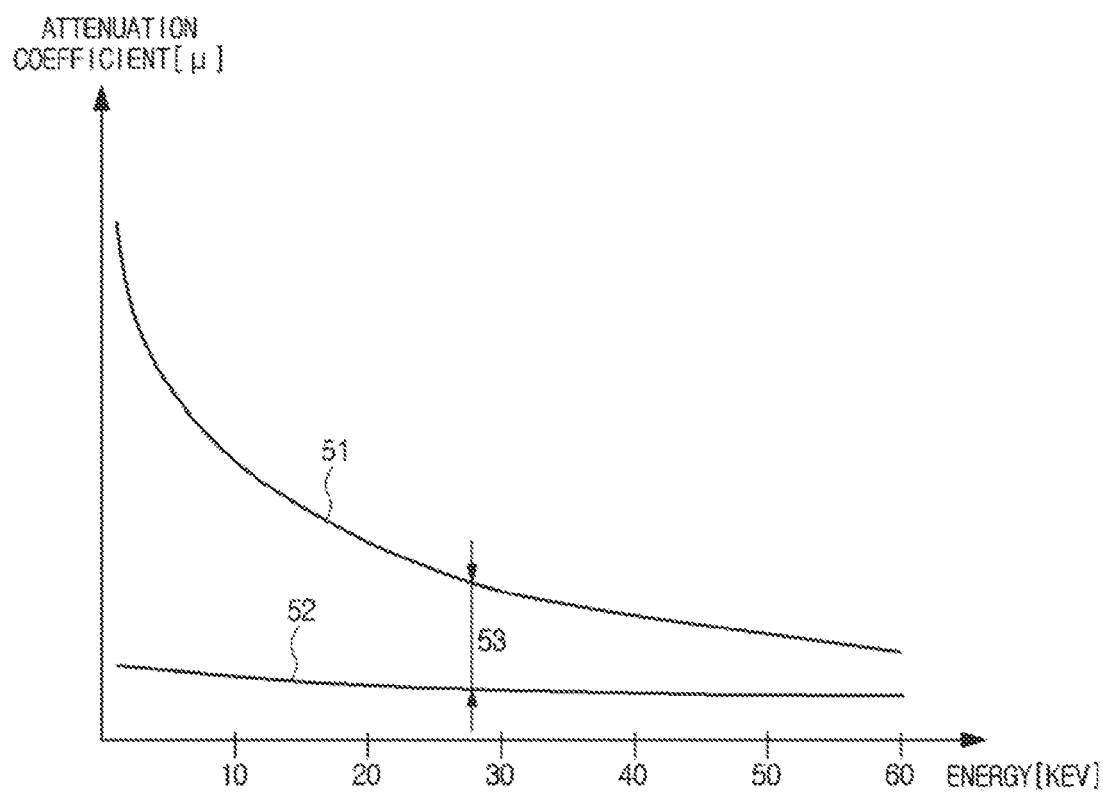
FIG. 10 is a graph showing an example of a difference between attenuation coefficients of different internal tissues in an object, according to an exemplary embodiment.

FIG. 10 is a graph showing an example of a difference between attenuation coefficients of different internal tissues in an object, according to an exemplary embodiment.

In FIG. 10, a reference number 51 represents a graph showing a change of a general attenuation coefficient with respect to a change in energy of bone among internal tissues of an object ob, a reference number 52 represents a graph showing a change of a general attenuation coefficient with respect to a change in energy of soft tissue among the internal tissues of the object ob, and a reference number 53 represents a difference between the attenuation coefficient of bone and the attenuation coefficient of soft tissue at predetermined energy.

Generally, the greater the difference between attenuation coefficients of different internal tissues of an object, the higher the image contrast. However, the qualities of X-ray images formed by X-rays are not dependent only on energy band, radiolucency, or intensity of X-rays. Since attenuation coefficients of bone and soft tissue are different enough to satisfy contrast required for X-ray images over a wide band of energy (for example, an energy band ranging from 10 Kev to 40 Kev), as shown in FIG. 10, a predetermined energy band (for example, an energy band ranging from 30 Kev to 40 Kev) may be used to obtain sufficient contrast of bone and soft tissue in X-ray images.

However, if attenuation coefficients of internal tissues of an object have similar characteristics, an energy band of X-rays influences image quality. The characteristics of an attenuation coefficient refers to a change of an attenuation coefficient with respect to a change of energy, as described above. For example, when X-rays of an energy band that is higher than a predetermined energy band (for example, an energy band of 20 Kev or more) are used to acquire an X-ray image of a patient's breast composed of soft tissues, such as microcalcification tissue, glandular tissue, adipose tissue, mass, or fibrous tissue, the soft tissues may be not easily distinguished from each other in the X-ray image.

The image analyzing unit 250 (see FIG. 2) may determine the kinds of tissues displayed in an image frame, based on unique attenuation coefficients of the individual tissues.

Figure 11:
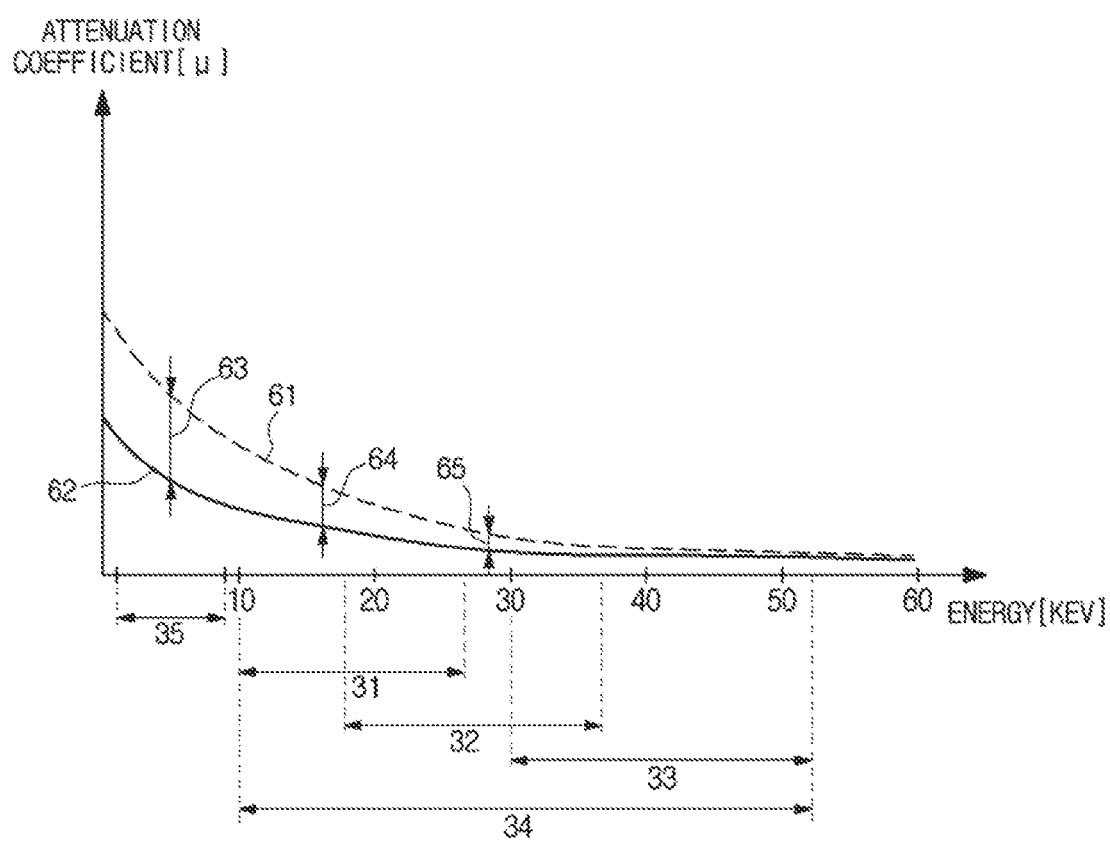
FIG. 11 is a graph showing another example of a difference between attenuation coefficients of different internal tissues in an object, according to another exemplary embodiment.

FIG. 11 is a graph showing another example of a difference between attenuation coefficients of different internal tissues in an object, according to another exemplary embodiment.

FIG. 11 shows a difference between attenuation coefficients of different internal soft tissues in an object. In FIG. 11, a reference number 61 represents a graph showing a change of an attenuation coefficient with respect to a change in energy of a first soft tissue in the object ob, a reference number 62 represents a graph showing a change of an attenuation coefficient with respect to a change in energy of a second soft tissue in the object ob, a reference number 63 represents a difference between attenuation coefficients of the first and second soft tissues at energy in an energy band 35, a reference number 64 represents a difference between attenuation coefficients of the first and second soft tissues at energy in another energy band 31, and a reference number 65 represents a difference between attenuation coefficients of the first and second soft tissues at energy in another energy band 32.

As shown in FIG. 11, in order to enhance contrast between the first and second soft tissues in the object ob, a method and apparatus according to an exemplary embodiment use X-rays having the energy band 35 in which attenuation coefficients of the first and second soft tissues shows a great difference.

However, using a low energy band (for example, the energy band 35 of FIG. 11) may have limitations due to physical characteristics of the low energy band and a dose limit of X-rays. For example, since X-rays of a low energy band (for example, the energy band 35 of FIG. 11) have lower radiolucency than X-rays of a high energy band (for example, the energy band 32 of FIG. 11), irradiating a dose of X-rays exceeding a dose limit may be needed in order to generate a high intensity of X-rays, which may be a practical impossibility.

By estimating X-ray data corresponding to X-rays of an energy band which has not actually been generated, based on X-ray data corresponding to X-rays of different energy bands that have actually been generated, it is possible to enhance contrast of an X-ray image. Referring to FIG. 11, by estimating X-ray data corresponding to X-rays of the energy band 35, which has never actually been detected by the X-ray detector 12 (see FIG. 1), based on X-ray data corresponding to X-rays of the energy band 31 and X-ray data corresponding to X-rays of the energy band 32, which have been transmitted through the object ob, it is possible to significantly enhance contrast between internal soft tissues of the object ob.

The image analyzing unit 250 (see FIG. 2) may determine the kinds of tissues displayed in an image frame, based on the unique attenuation coefficients of the soft tissues.

Hereinafter, a method of analyzing motions of tissues in an object and correcting an image frame according to the analyzed motions of the tissues, according to an exemplary embodiment, will be described with reference to FIGS. 12, 13, and 14.

FIG. 12 is a view for describing the concept of a method of separating, correcting, and combining image frames in the X-ray imaging apparatus 1, according to an exemplary embodiment.

Referring to FIGS. 1, 2, and 12, the X-ray detector 150 may convert X-rays detected successively into electrical X-ray data, and convert the electrical X-ray data into image signals to generate a plurality of image frames 72. Thereafter, the image analyzing unit 250 may compare the plurality of image frames 72 to each other to analyze kinds and motions of tissues displayed in a current image frame 71.

More specifically, the image analyzing unit 250 may calculate motion vectors of the individual tissues using a block matching algorithm and optical flow.

Details about the block matching algorithm will be described in detail with reference to FIG. 13, later, and details about the optical flow will be described in detail with reference to FIG. 14, later.

After the image analyzing unit 250 analyzes the motions of the tissues displayed in the image frame 71, the image separating unit 300 may extract a first tissue image 73 without motion based on the motions of the tissues. As illustrated in FIG. 12, the image separating unit 300 may extract the first tissue image 73 including spine and ribs without motion from the plurality of image frames 72.

Thereafter, the image separating unit 300 may extract the remaining image except for the first tissue image 73 from the current image frame 71, as a second tissue image 74, and assume the second tissue image 74 is an image with motion.

Then, the image corrector 370 may multiply an intensity matrix of the second tissue image 74 by a motion transform matrix acquired by the function acquiring unit 380 to raise the left part of the second tissue image 74 and lower the right part of the second tissue image 74, thereby generating a corrected second tissue image 75.

Finally, the image combining unit 390 may combine the first tissue image 73 with the corrected second tissue image 75 to generate a corrected current image frame 76, and display the corrected current image frame 76 on the display 660.

The process of separating, correcting, and combining images may be repeatedly performed until it is determined that no motion of tissues is detected from the plurality of image frames 72 or that the corrected current image frame 76 is identical to the plurality of image frames 72.

Also, since a process of analyzing the kinds and motions of the tissues in the plurality of image frames 72 requires a large amount of computation, according to an exemplary embodiment, the image separating unit 300 may apply a different correction to only the second tissue image 74 in the state of fixing the first tissue image 73 and the second tissue image.

More specifically, the X-ray imaging apparatus 1 may generate the corrected current image frame 76 by correcting and combining the tissue images using Equation (1), below.

$$\Sigma_I W_{k,I} f_I \quad (1)$$

Equation (1) is used by the image correcting unit 370 to correct the plurality of tissue images and combine the corrected tissue images. In Equation (1), a variable $W_{k,I}$ represents a motion transform matrix for a first tissue image in a k-th photographed image frame, and $f_I$ represents an intensity matrix of the first tissue image.

According to Equation (1), the image correcting unit 370 may multiply a motion transform matrix which is a correction function for each tissue image calculated by the function acquiring unit 380 based on the kinds and motions of the tissues analyzed by the image analyzing unit 250, by an intensity matrix of the tissue image extracted by the image separating unit 300. Then, the image combining unit 390 may combine all of the corrected tissue images to generate the corrected current image frame 76.

Herein, the motion transform matrix of the tissue image without motion among the motion transform matrices is an identity matrix to maintain an intensity matrix of the corresponding tissue image. Also, the motion transform matrix of the tissue image with motion may be a matrix acquired by the function acquiring unit 380 such that the elements of the intensity matrix of the corresponding tissue image are located at desired locations without changing the element values of the intensity matrix.

$$\Sigma_k \| y_k - \Sigma_I W_{k,I} f_I \| \quad (2)$$

Equation 2 is used by the image processor 350 to perform operations of correcting and combining the image frames until the corrected current image frame converges on the current image frame. In Equation (2), $y_k$ represents an intensity matrix of a k-th photographed image frame.

The image processor 350 may subtract an intensity matrix of the corrected current image frame 76 from the intensity matrix of the k-th photographed image frame. The image processor 350 may apply the subtraction operation to all of the plurality of image frames 72, and then add the resultant values. Adding k resultant values according to Equation (2) results in a value representing whether or not the corrected current image frame 76 converges on the plurality of image frames 72. If the value is equal to or smaller than a predetermined value, the X-ray imaging apparatus 1 may determine that the object ob has no motion, and stop performing the operation of correcting and combining image frames.

Figure 13:
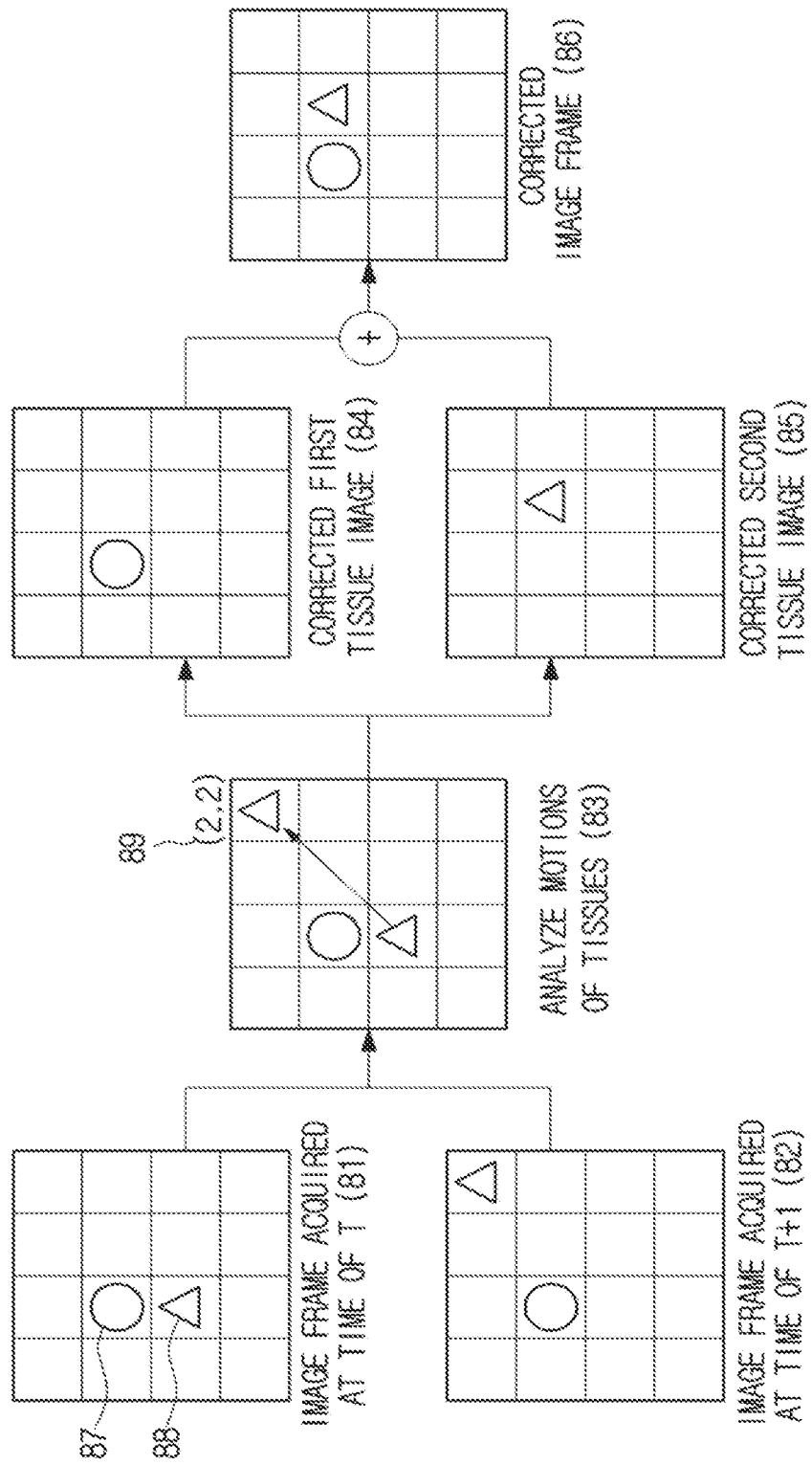
FIG. 13 is a view for describing the concept of a method of analyzing and correcting a motion of each tissue using a block matching algorithm, according to an exemplary embodiment.

FIG. 13 is a view for describing the concept of a method of analyzing and correcting a motion of each tissue using a block matching algorithm, according to an exemplary embodiment.

The block matching algorithm is a method of dividing an image frame into a plurality of blocks each having a constant size, and representing all pixels in each block by motion vectors. In order to calculate motion vectors, the image analyzing unit 250 may move blocks of the previous frame in units of a pixel to detect a block that is most similar to a current block from the previous frame.

For example, as shown in FIG. 13, an object ob displayed in an image frame may include a first tissue 87 and a second tissue 88. In an image frame 81 acquired at a time of t, the first tissue 87 is located at a location of I22, and the second tissue 88 is located at a location of I32. Also, in an image frame 82 acquired at a time of t+1, the first tissue 87 is located at the location of I22, and the second tissue 88 is located at a location of I14.

In this case, the motion analyzer 270 (see FIG. 2) may determine that the first tissue 87 has no motion and the second tissue 88 has motion through the block matching algorithm. More specifically, the motion analyzer 270 may detect a location having a similar intensity to that of the first tissue 87 in the image frame 81 acquired at the time of t, from locations I11 to I44 of the image frame 82 acquired at the time of t+1 through one-to-one matching to determine that the first tissue 87 is located at the same location of I22 in both the image frame 81 acquired at the time of t and the image frame 82 acquired at the time of t+1, thereby determining that the first tissue 87 has no motion.

Also, the motion analyzer 270 may detect a location having a similar intensity to that of the second tissue 88 in the image frame 81 acquired at the time of t, from the locations I11 to I44 of the image frame 82 acquired at the time of t+1 through one-to-one matching. Thereby, the motion analyzer 270 may determine that the second tissue 88 is located at the location I32 in the image frame 81 acquired at the time of t and at the location I14 in the image frame 82 acquired at the time of t+1 to determine that the second tissue 88 has moved by a distance of (2, −2) during a time period from t to t+1.

Thereafter, the image separating unit 300 (see FIG. 2) may extract a first tissue image and a second tissue image from the image frame 81 acquired at the time of t, and the image correcting unit 370 (see FIG. 2) may multiply an intensity matrix of the first tissue image by an identity matrix to generate a corrected first tissue image 84. Then, the image correcting unit 370 may multiply an intensity matrix of the second tissue image by a motion transform matrix to generate a corrected second tissue image 85 such that the second tissue 88 is located at a location of I23.

Finally, the image combining unit 390 may combine the corrected first tissue image 84 with the corrected second tissue image 85 to generate a corrected image frame 86.

Figure 14:
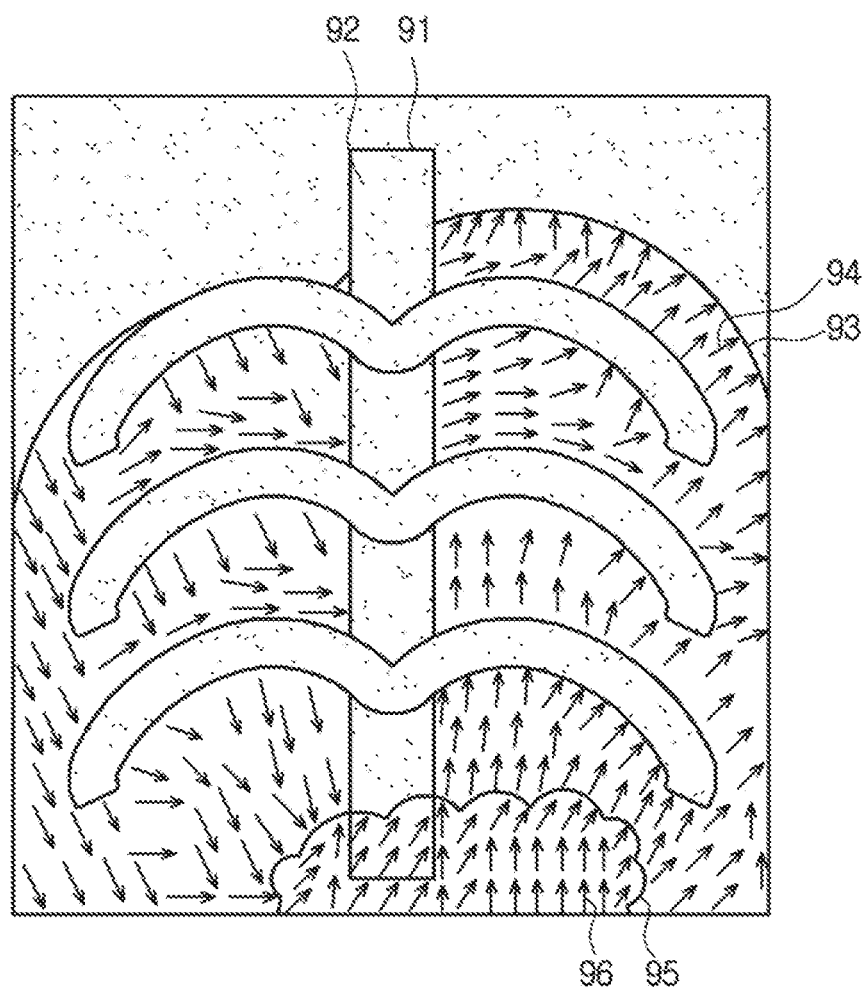
FIG. 14 is a view for describing the concept of a method of analyzing a motion of each tissue using optical flow, according to an exemplary embodiment.

FIG. 14 is a view for describing the concept of a method of analyzing motion of each tissue using optical flow, according to an exemplary embodiment.

The optical flow is a motion analysis method of blocking feature points in image frames acquired at a time of t and at a time of t+1, and converting the blocks into intensity matrices to represent changes of the individual feature points as motion vectors.

That is, the image analyzing unit 250 (see FIG. 2) may analyze movement locations of feature points between an image frame acquired at a time of t and an image frame acquired at a time of t+1 to thereby analyze motions of individual tissues.

For example, as shown in FIG. 14, the image analyzing unit 250 may determine that spine and ribs tissues 91 have no motion through motion vectors 92 of bone tissue. Also, the image analyzing unit 250 may determine that the right part of a first soft tissue 93 of the chest has moved toward the lower right part of the chest, and the left part of the first soft tissue 93 has moved toward the upper right part of the chest, based on motion vectors 94 of the first soft tissue 93. Also, the image analyzing unit 250 may determine that a second tissue 95 of the chest has moved toward the upper part of the chest, based on motion vectors 96 of the second soft tissue 95.

Hereinafter, a method of controlling an X-ray imaging apparatus, according to an exemplary embodiment, will be described with reference to FIG. 15.

Figure 15:
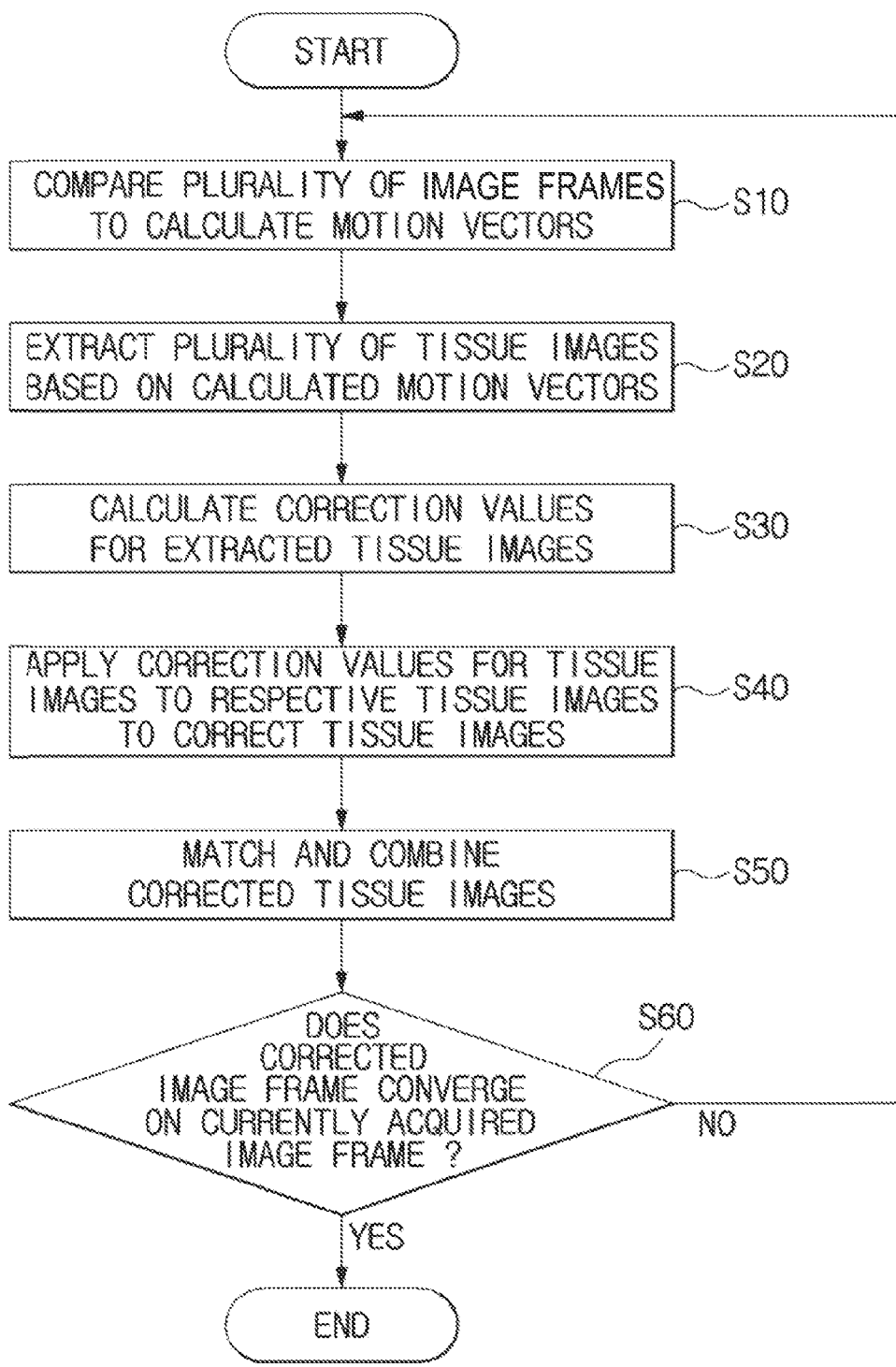
FIG. 15 is a flowchart illustrating a method of controlling an X-ray imaging apparatus to separate, correct and combine a plurality of frame images to acquire a corrected frame image, according to an exemplary embodiment.

FIG. 15 is a flowchart illustrating a method of separating, correcting, and combining a plurality of image frames to acquire a corrected image frame, according to an exemplary embodiment.

First, the X-ray imaging apparatus may compare a plurality of fame images to calculate motion vectors of individual tissues, through an image analyzing unit, in operation S10.

Then, the X-ray imaging apparatus may extract a plurality of tissue images from the plurality of image frames, based on the calculated motion vectors of the individual tissues, through an image separating unit, in operation S20.

Thereafter, the X-ray imaging apparatus may calculate correction values for the extracted tissue images, through a function acquiring unit, in operation S30, and apply the correction values for the tissue images to the respective tissue images to correct the tissue images, through an image correcting unit, in operation S40.

Then, the X-ray imaging apparatus may match the corrected tissue images, and combine the corrected tissue images to generate a corrected image frame, in operation S50.

Thereafter, the X-ray imaging apparatus may determine whether the corrected image frame converges on a currently acquired image frame, in operation S60.

If the X-ray imaging apparatus determines that the corrected image frame does not converge on the currently acquired image frame, the X-ray imaging apparatus may again perform operation S10 to operation S50.

Meanwhile, if the X-ray imaging apparatus determines that the corrected image frame converges on the currently acquired image frame, the X-ray imaging apparatus may stop performing the operation of correcting and combining the image frames.

According to the X-ray imaging apparatus and the control method for the same, as described above, by separating a plurality of image frames into a plurality of tissue images according to motions of tissues, performing appropriate correction on each tissue image, and then combining the corrected tissue images, instead of entirely correcting the plurality of image frames, a corrected image frame may be acquired.

Although a few exemplary embodiments have been shown and described, it would be appreciated by those skilled in the art that changes may be made in these exemplary embodiments without departing from the principles and spirit of the exemplary embodiments, the scope of which is defined in the claims and their equivalents.

What is claimed is:

1. An X-ray imaging apparatus comprising:
   an X-ray generator configured to irradiate the X-rays onto an object;
   an X-ray detector configured to detect the X-rays transmitted through the object, and to generate an image frame; and
   an image processor configured to separate a first tissue image having a small amount of motion of a tissue, the small amount of motion being smaller than a threshold amount of motion, and a second tissue image having a large amount of motion of a tissue, the large amount of motion being larger than the small amount of motion, from a plurality of image frames about a plurality of tissues which are classified according to the motions of tissues, and to extract the separated first and second tissue images, and to correct the second tissue image according to the large amount of motion of the tissue.

2. The X-ray imaging apparatus according to claim 1, wherein the image processor is configured to estimate the large amount of motion of the tissue displayed in the second tissue image, and correct the second tissue image according to the estimated motion of the tissue.

3. The X-ray imaging apparatus according to claim 1, wherein the image processor is configured to combine the corrected second tissue image with the first tissue image to generate a corrected image frame.

4. The X-ray imaging apparatus according to claim 1, wherein the image processor is configured to extract the second tissue image from an image frame of the plurality of image frames, and extract the first tissue image from another image frame of the plurality of image frames.

5. The X-ray imaging apparatus according to claim 1, wherein the image processor is configured to extract the second tissue image from an image frame of the plurality of image frames, and remove components of the second tissue image from another image frame of the plurality of image frames to extract the first tissue image.

6. The X-ray imaging apparatus according to claim 1, wherein the image processor is configured to compare the plurality of image frames to each other to analyze a plurality of motions of a plurality of tissues included in the plurality of image frames.

7. The X-ray imaging apparatus according to claim 6, wherein the image processor is configured to group the analyzed motions of the tissues into a plurality of groups according to predetermined criteria, and to extract a tissue image for each group, and
   to correct each tissue image using a predetermined correction value according to a group to which the tissue image belongs.

8. The X-ray imaging apparatus according to claim 6, wherein the image processor is configured to calculate a plurality of motion vectors of each tissue, and to convert, for each tissue, the motion vectors of the tissue into a motion transform matrix, and correct a tissue image of the tissue using the motion transform matrix.

9. The X-ray imaging apparatus according to claim 6, wherein the image processor is configured to analyze the motions of the tissues using pre-stored tissue data.

10. The X-ray imaging apparatus according to claim 6, wherein the image processor is configured to compare the corrected image frame to the plurality of image frames to analyze a motion of each tissue, and to correct a tissue image of each tissue according to the analyzed motion of the tissue, and to repeat the operations of comparing the corrected image frame and correcting the tissue image until the image processor determines that the tissue has no motion based on results of comparison between the corrected image frame and the plurality of image frames.

11. A control method to control an X-ray imaging apparatus, the control method comprising:
    separating a first tissue image having a small amount of motion of a tissue, the small amount of motion being smaller than a threshold amount of motion, and a second tissue image having a large amount of motion of a tissue, the large amount of motion being larger than the small amount of motion, from a plurality of image frames about plurality of tissues which are classified according to the motions of tissues;
    extracting the separated first and second tissue images; and
    correcting the second tissue image according to the large amount of motion of the tissue.

12. The control method according to claim 11, further comprising estimating the large amount of motion of the tissue displayed in the second tissue image,
    wherein the correcting of the second tissue image comprises correcting the second tissue image according to the estimated motion of the tissue.

13. The control method according to claim 11, further comprising combining the corrected second tissue image with the first tissue image to generate a corrected image frame.

14. The control method according to claim 11, wherein the extracting of the first tissue image comprises extracting the first tissue image from an image frame of the plurality of image frames, and the extracting of the second tissue image comprises extracting the second tissue image from another image frame of the plurality of image frames.

15. The control method according to claim 11, wherein the extracting of the second tissue image comprises extracting the second tissue image from an image frame of the plurality of image frames, and the extracting of the first tissue image comprises removing components of the second tissue image from another image frame of the plurality of image frames to extract the first tissue image.

16. The control method according to claim 11, further comprising comparing the plurality of image frames to each other to analyze a plurality of motions of a plurality of tissues included in the plurality of image frames.

17. The control method according to claim 15, further comprising grouping the analyzed motions of the tissues into a plurality of groups according to predetermined criteria,
    wherein the extracting of the first tissue image and the second tissue image comprises extracting a tissue image for each group, and
    the correcting of the second tissue image according to the large amount of motion of the tissue comprises correcting each tissue image using a predetermined correction value according to a group to which the tissue image belongs.

18. The control method according to claim 16, wherein the comparing of the plurality of image frames to each other to analyze the motions of the tissues comprises calculating a plurality of motion vectors of each tissue, and
    the correcting of the second tissue image according to the large amount of motion of the tissue comprises converting, for each tissue, the motion vectors of the tissue into a motion transform matrix, and correcting a tissue image of the tissue using the motion transform matrix.

19. The control method according to claim 16, wherein the comparing of the plurality of image frames to each other to analyze the motions of the tissues comprises analyzing the motions of the tissues using pre-stored tissue data.

20. The control method according to claim 16, further comprising:
- comparing the corrected image frame to the plurality of image frames to analyze a motion of each tissue, and re-extracting one or more tissue images, and
- correcting the tissue images according to the analyzed motion of each tissue, and combining the corrected tissue images to re-produce a corrected image frame,
- wherein the comparing and the correcting are repeated until it is determined that the tissue has no motion based on the results of comparison between the corrected image frame and the plurality of image frames.

* * * * *